US012790345B2

(12) United States Patent
Muthusamy et al.

(10) Patent No.: US 12,790,345 B2
(45) Date of Patent: Nov. 10, 2026

(54) SOLID STATE FORMS OF TRILACICLIB AND OF TRILACICLIB SALTS

(71) Applicant: ASSIA CHEMICAL INDUSTRIES LTD., Tel Aviv (IL)

(72) Inventors: Anantha Rajmohan Muthusamy, Sivakasi (IN); Amit Singh, Greater Noida (IN); Meenakshi Sundaram Somasundaram, Virudu Nagar DT (IN); Yogesh Dhananjay Wagh, Badlapur (E) Thane (IN); Parven Kumar Luthra, Noida (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 659 days.

(21) Appl. No.: 18/030,547

(22) PCT Filed: Oct. 8, 2021

(86) PCT No.: PCT/US2021/054110
§ 371 (c)(1),
(2) Date: Apr. 6, 2023

(87) PCT Pub. No.: WO2022/076779
PCT Pub. Date: Apr. 14, 2022

(65) Prior Publication Data

US 2023/0374028 A1 Nov. 23, 2023

(30) Foreign Application Priority Data

| | | |
|---|---|---|
| Oct. 8, 2020 | (IN) | 202011043937 |
| Nov. 6, 2020 | (IN) | 202011048631 |
| Dec. 7, 2020 | (IN) | 202011053223 |

(51) Int. Cl.
*C07D 487/20* (2006.01)

(52) U.S. Cl.
CPC ........ *C07D 487/20* (2013.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 8,598,186 B2 * | 12/2013 | Tavares ................ | C07D 519/00 544/244 |
| 10,988,479 B1 * | 4/2021 | Schneider .............. | A61K 47/02 |
| 2020/0123168 A1 | 4/2020 | Smith et al. | |

FOREIGN PATENT DOCUMENTS

| | | |
|---|---|---|
| WO | 2012061156 A1 | 5/2012 |
| WO | 2016126889 A1 | 8/2016 |

(Continued)

OTHER PUBLICATIONS

Berge et al., J. Pharmaceutical Sciences, 66(1), 1-19 (Year: 1977).*

(Continued)

*Primary Examiner* — Adam C Milligan
*Assistant Examiner* — Jason M. Nolan
(74) *Attorney, Agent, or Firm* — Carter, DeLuca & Farrell LLP

(57) ABSTRACT

The present disclosure encompasses solid state forms of Trilaciclib and of Trilaciclib salts, in embodiments crystalline polymorphs of Trilaciclib and of Trilaciclib salts, processes for preparation thereof, and pharmaceutical compositions thereof.

16 Claims, 17 Drawing Sheets

XRPD of Trilaciclib Form TT1)

(56) References Cited

FOREIGN PATENT DOCUMENTS

| | | | |
|---|---|---|---|
| WO | 2018005865 | A1 | 1/2018 |
| WO | 2021257587 | A1 | 12/2021 |

OTHER PUBLICATIONS

Official Action issued in corresponding European Application No. 21801775.4 dated May 14, 2024 (4 pages).

International Search Report and Written Opinion of the International Searching Authority issued in corresponding application PCT/US2021/054110 mailed Mar. 14, 2022 (19 pages).

* cited by examiner

Figure 1: XRPD of Trilaciclib Form TT1)
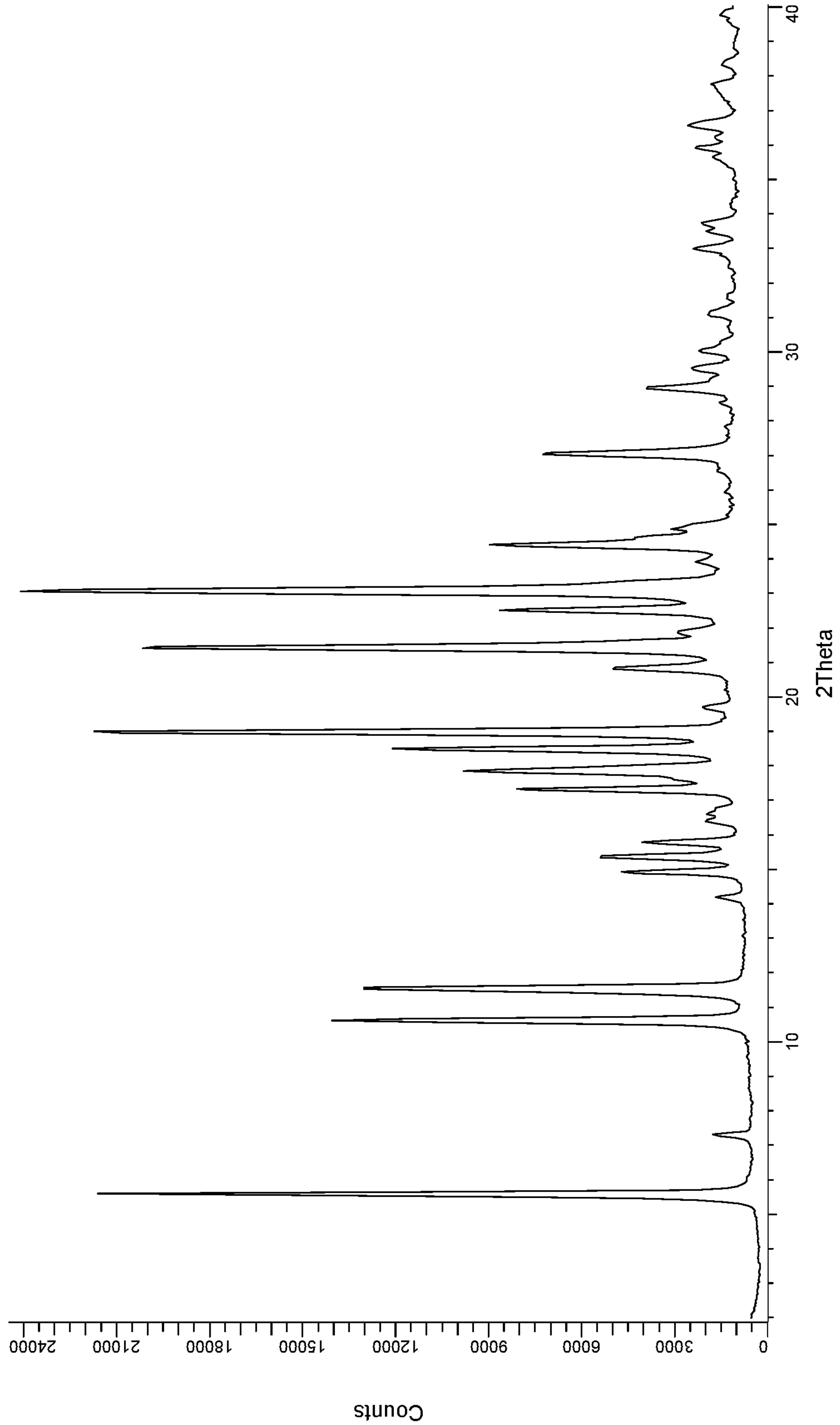

Figure 2: XRPD of Trilaciclib Form TT2
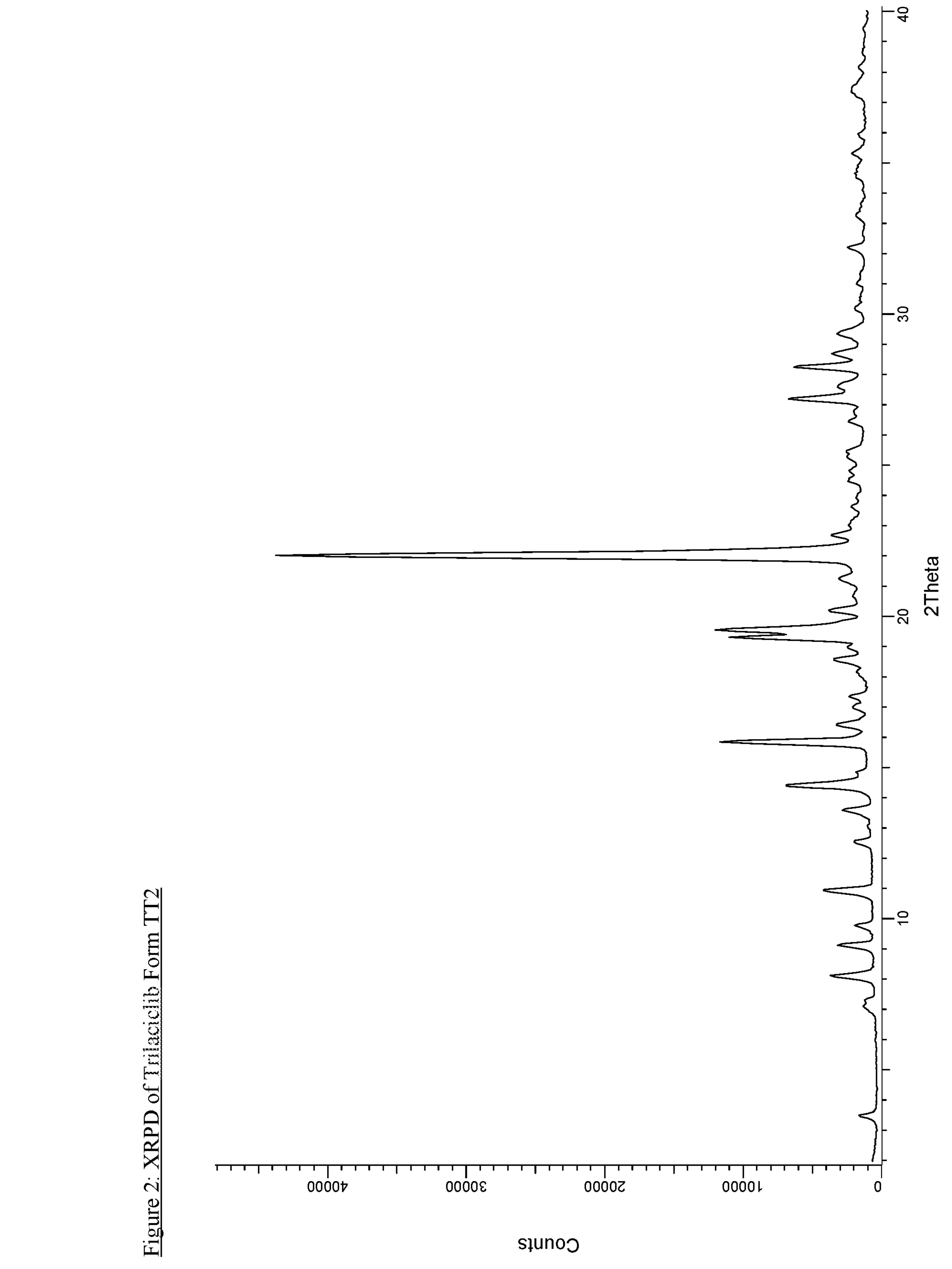

Figure 3: XRPD of Trilaciclib Form TT3
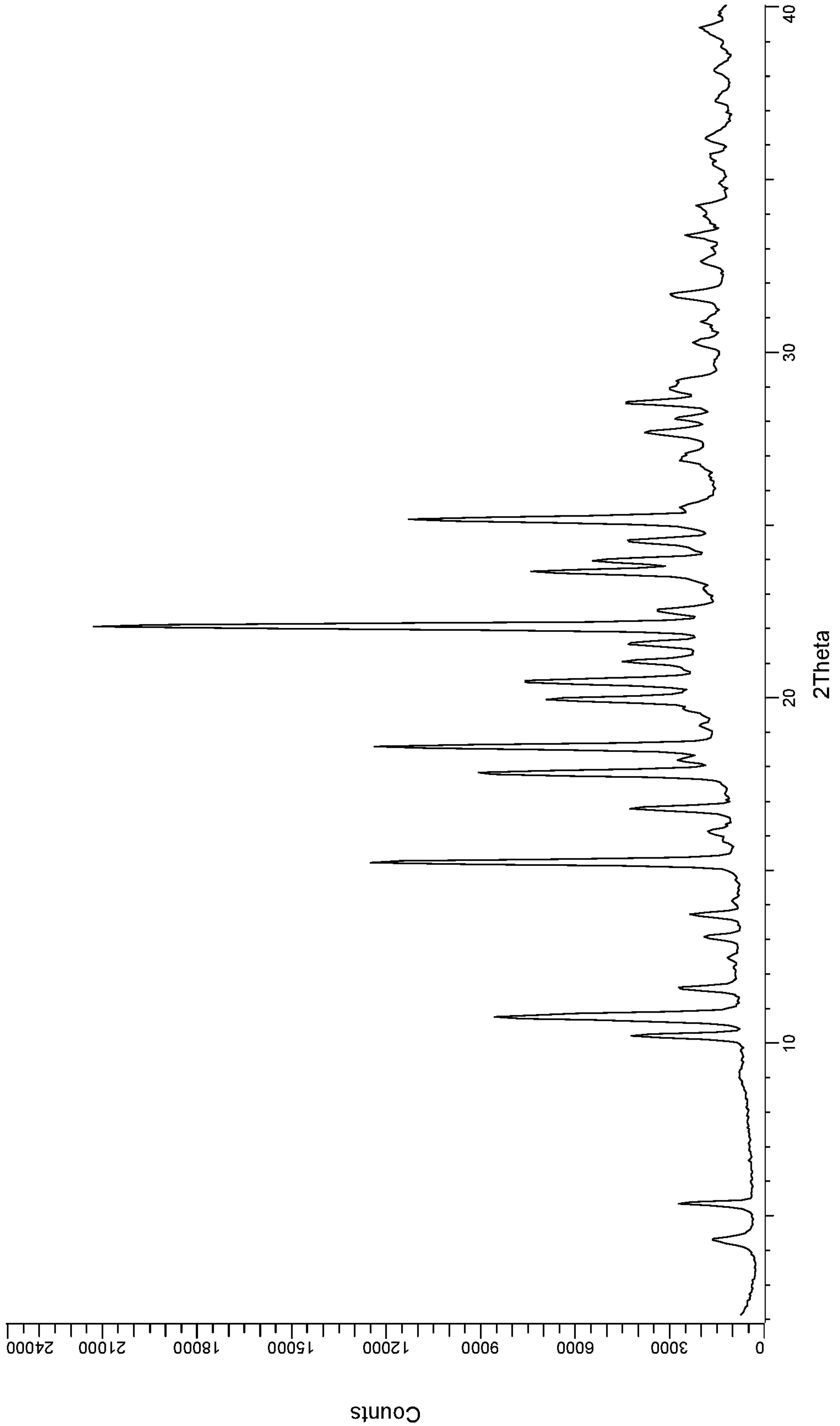

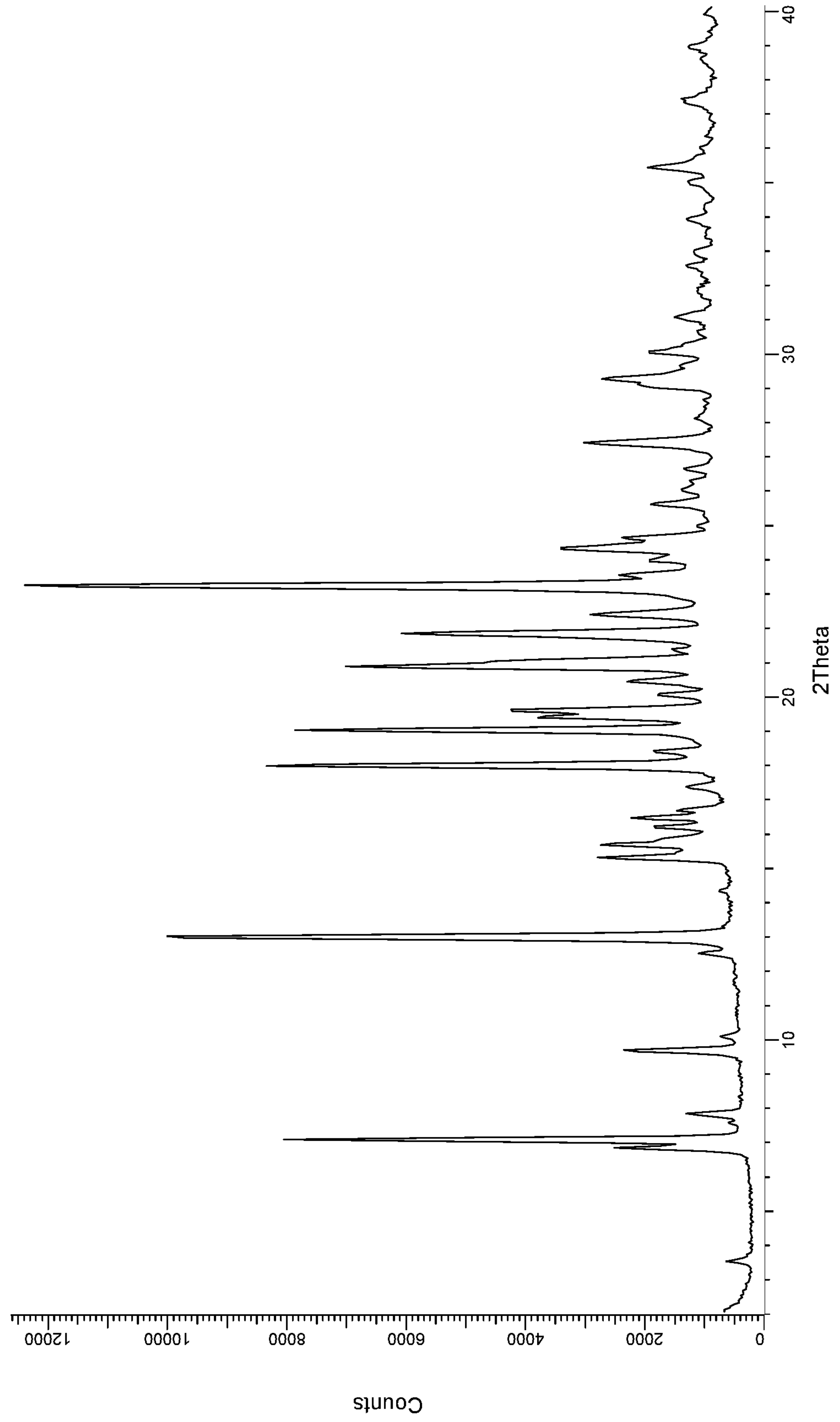
Figure 4: XRPD of Trilaciclib Form TT4

Figure 5: XRPD of Trilaciclib trifluoroacetate salt Form TTFA1
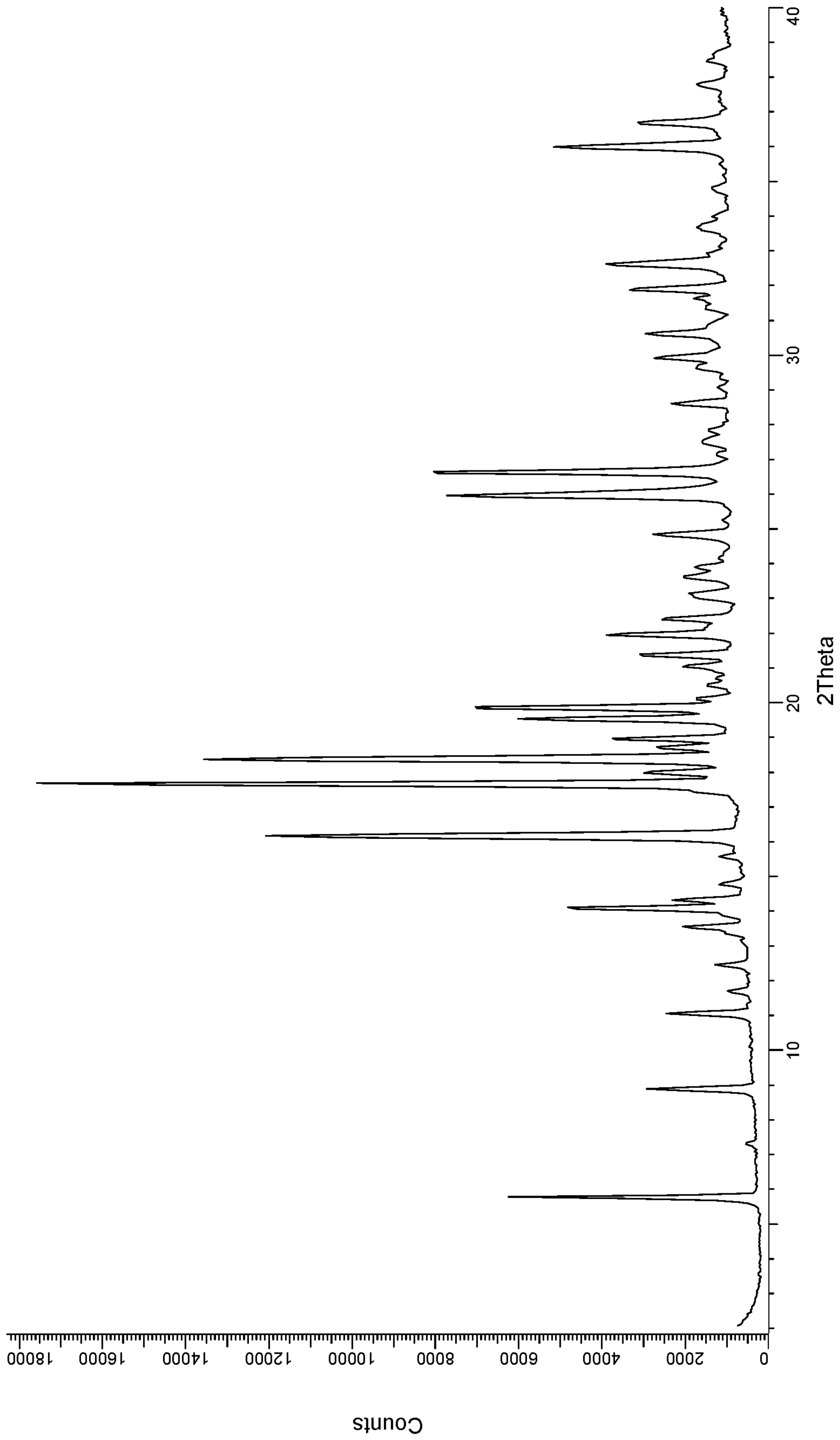

Figure 6: XRPD of Trilaciclib dihydrochloride salt Form THCl1
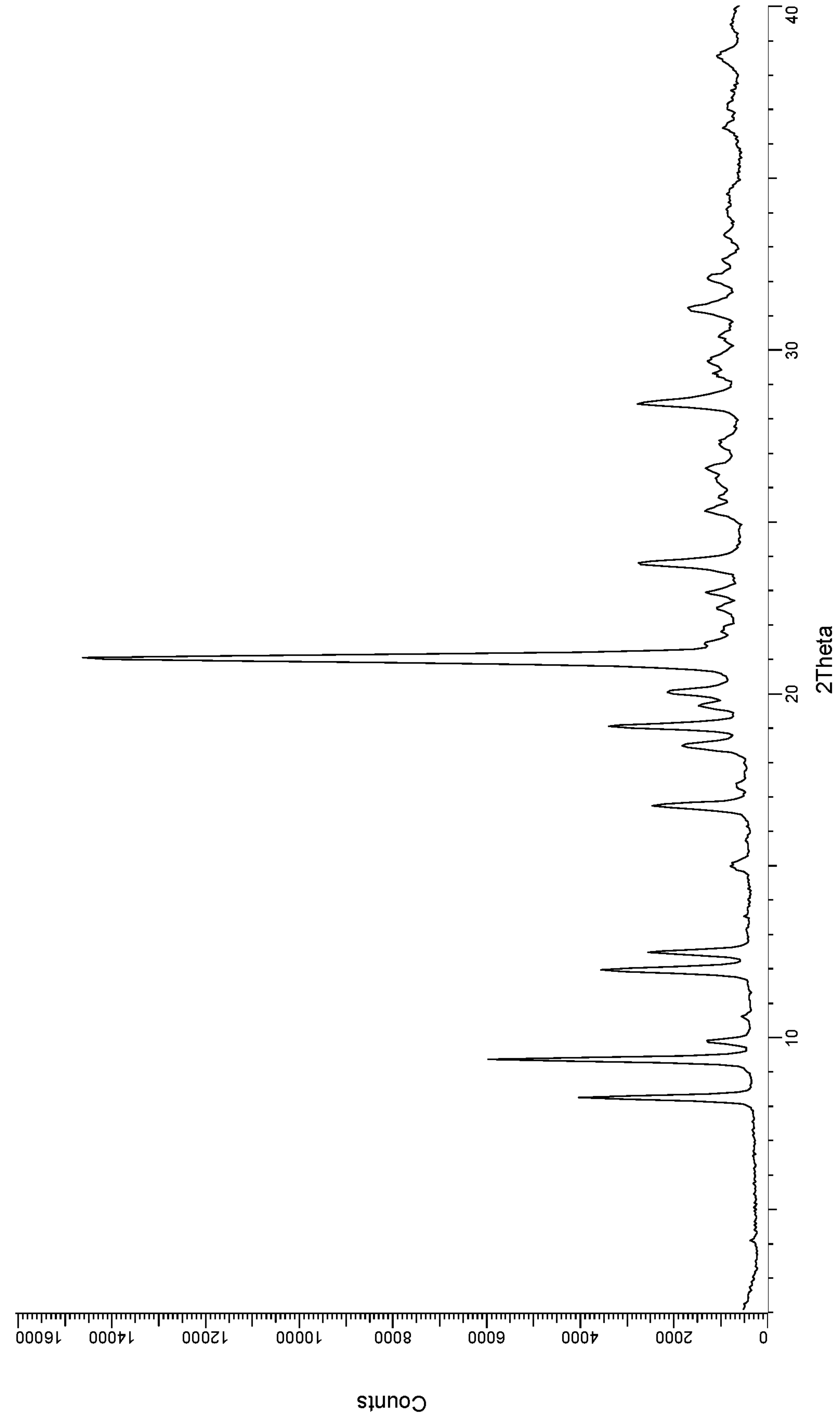

Figure 7: XRPD of Trilaciclib hydrochloride salt Form THCl
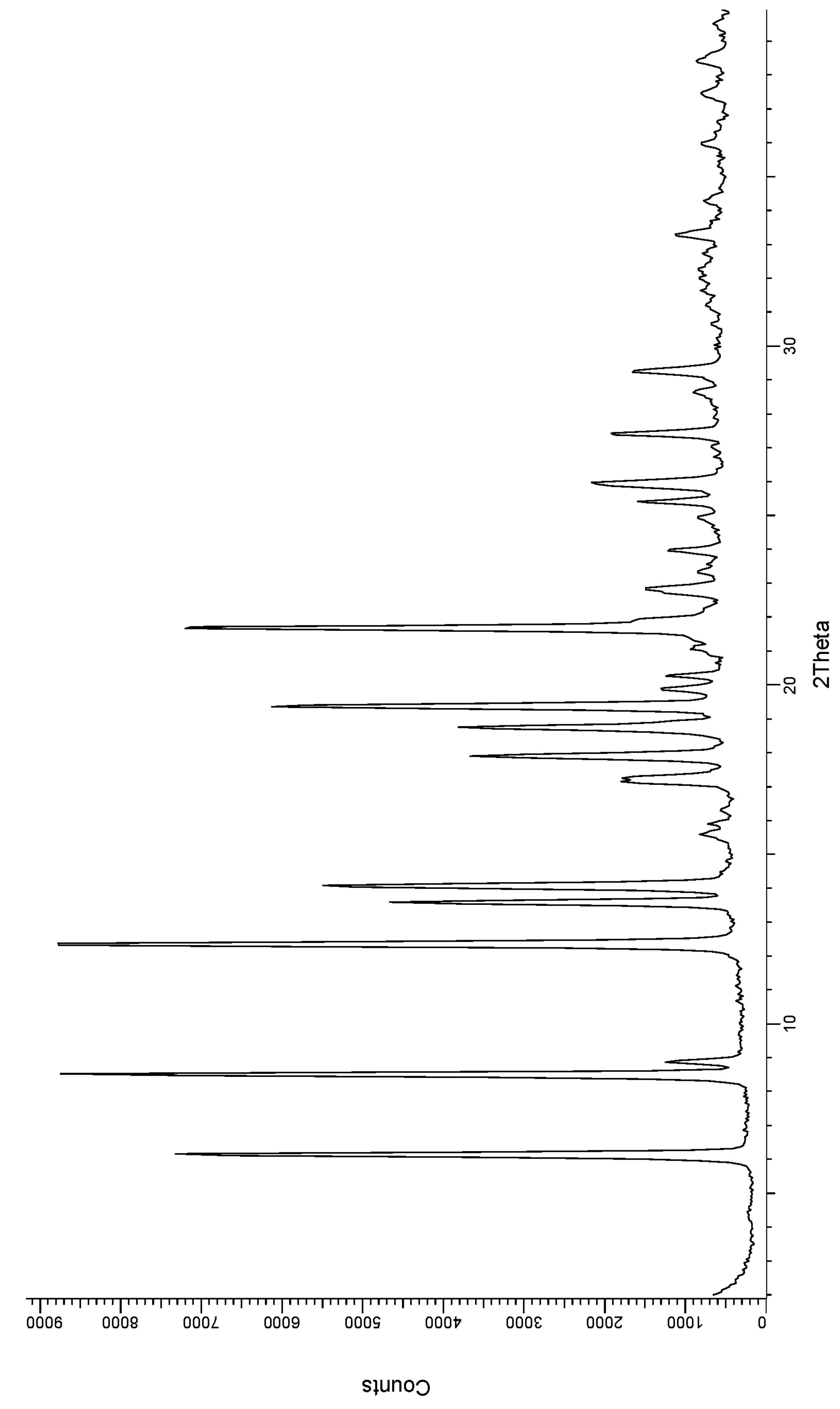

Figure 8: XRPD of Trilaciclib citrate salt Form TCT1
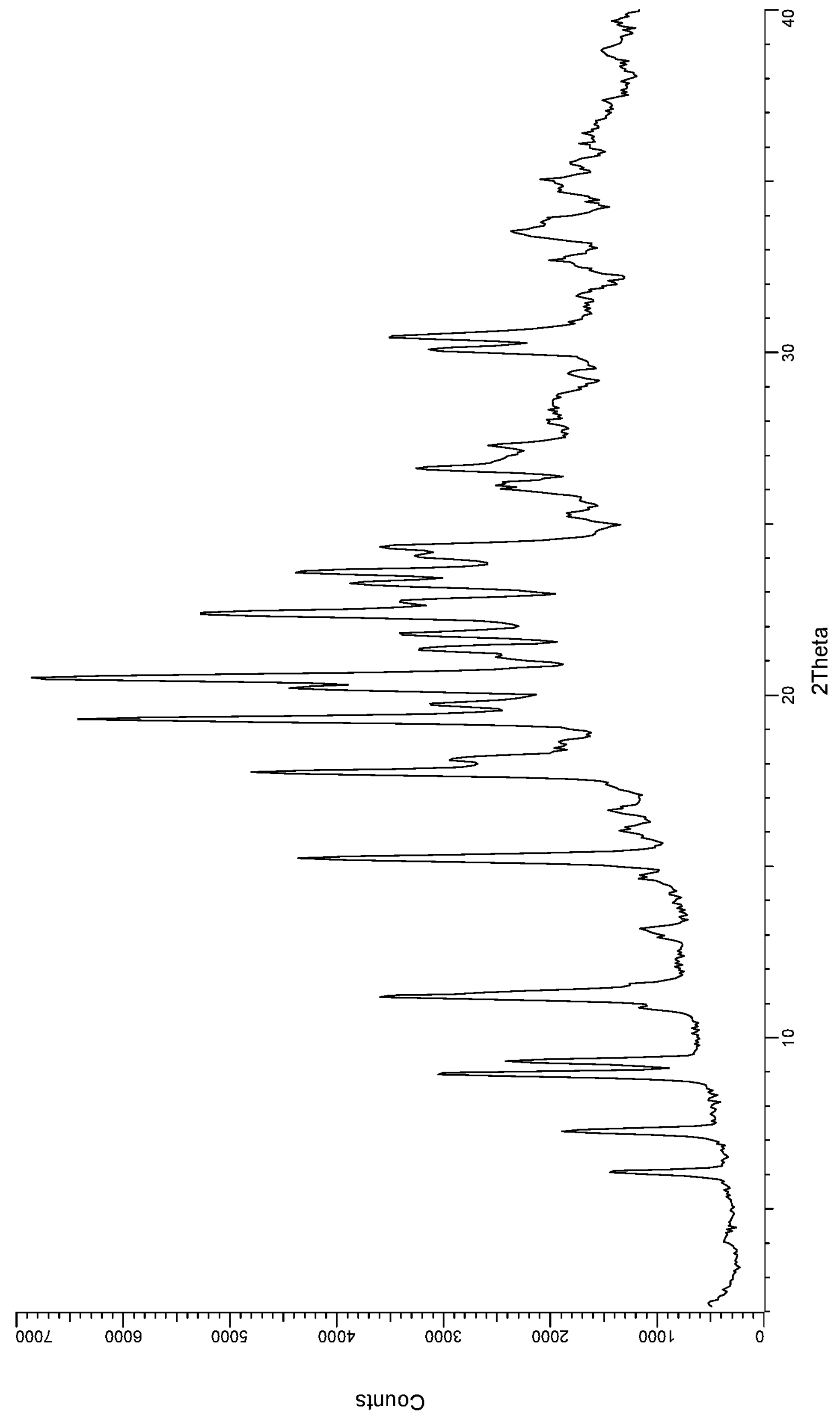

Figure 9: XRPD of Trilaciclib sulphate salt Form TS1
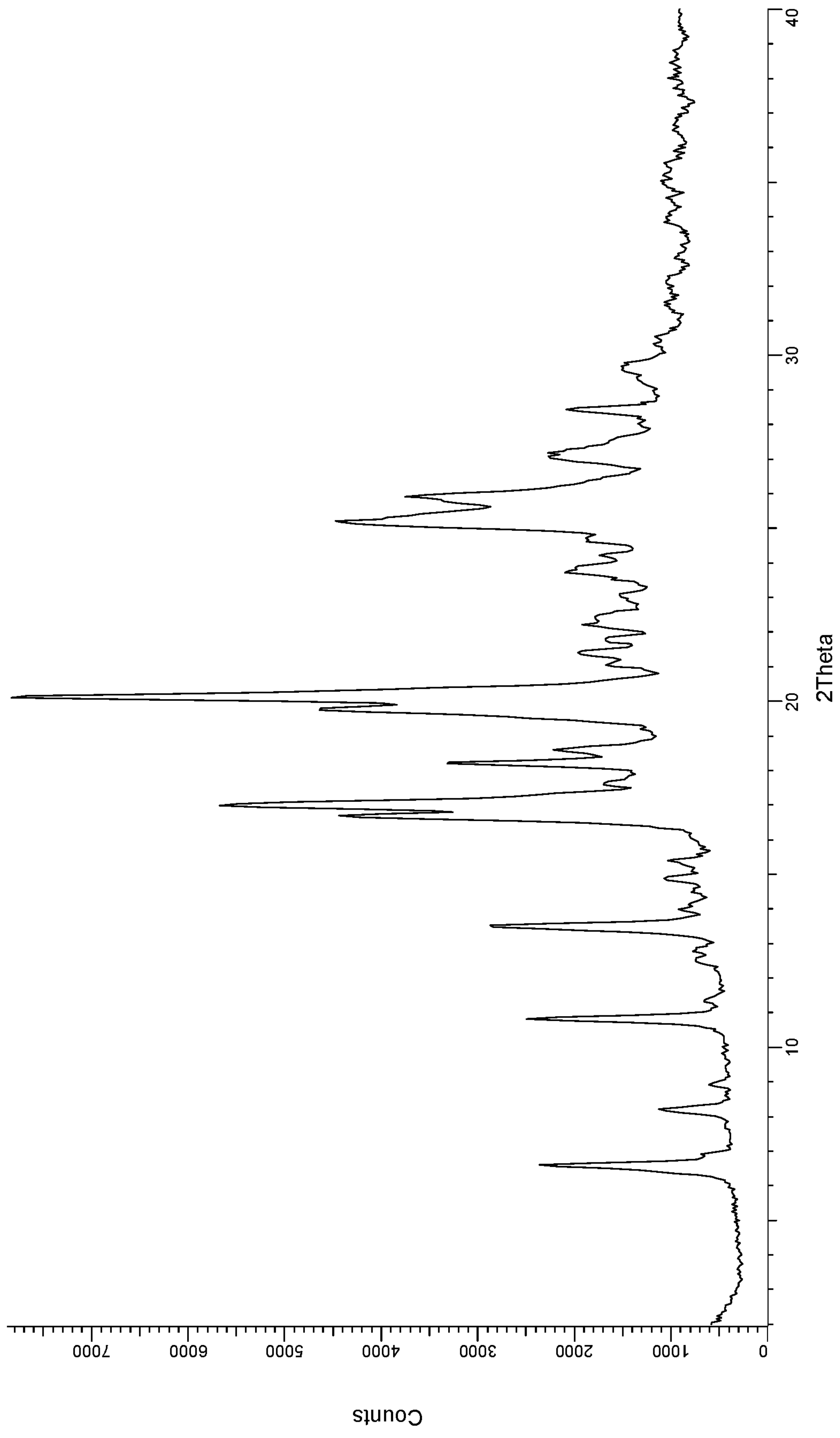

Figure 10: XRPD of Trilaciclib mesylate salt Form TMSA1
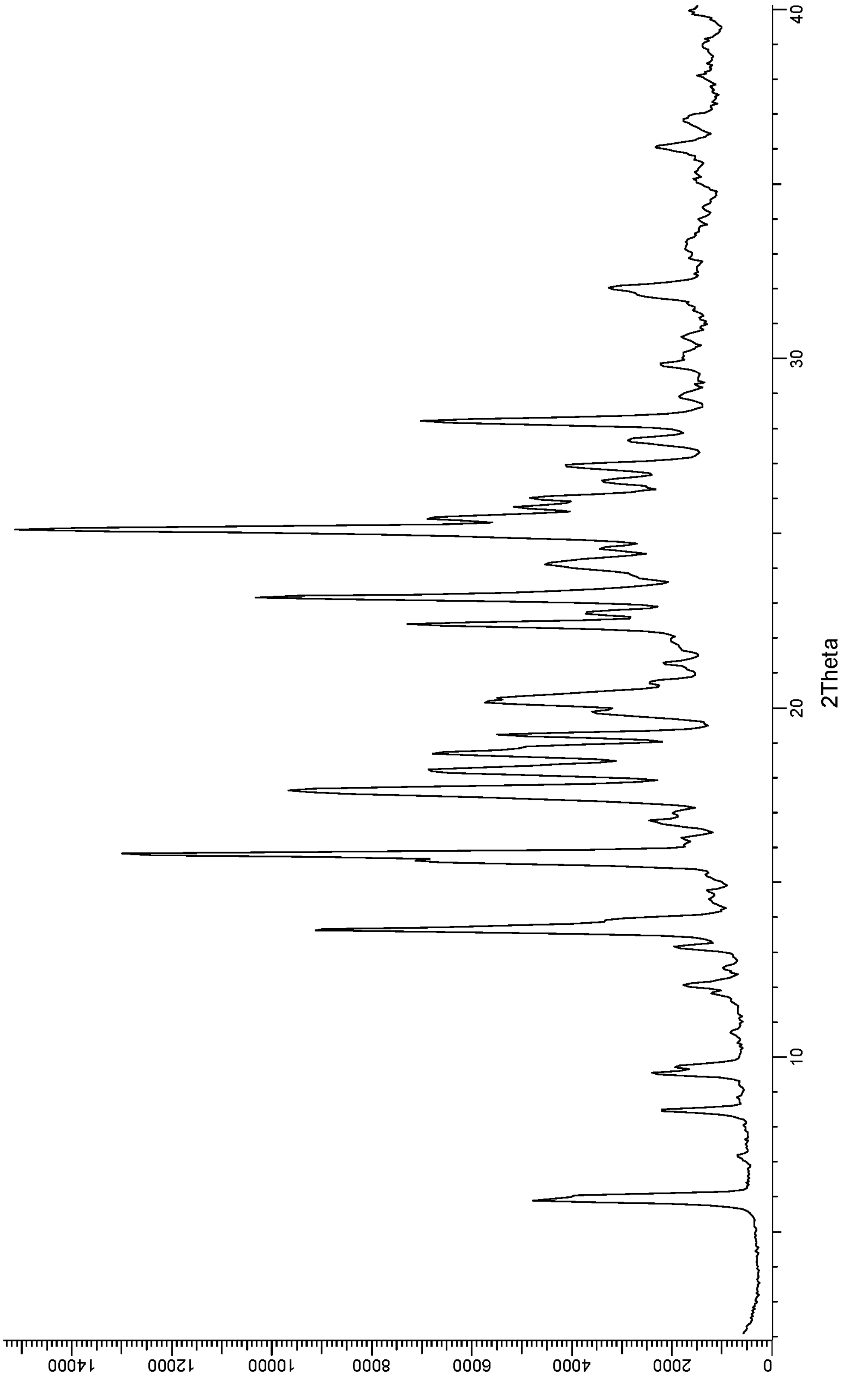

Figure 11: XRPD of Trilaciclib besylate salt Form TBSA1
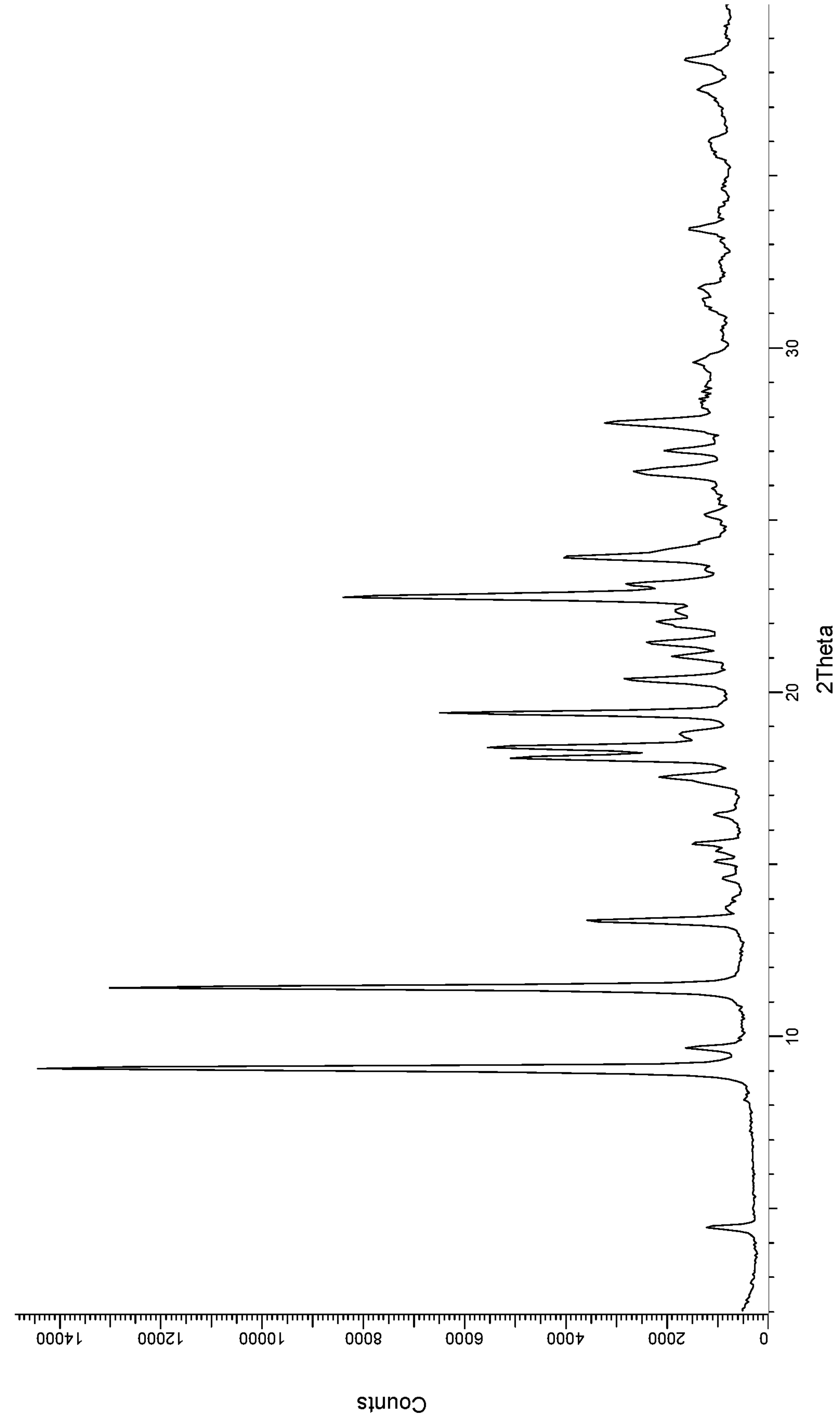

Figure 12: XRPD of Trilaciclib dihydrochloride salt Form THCl2
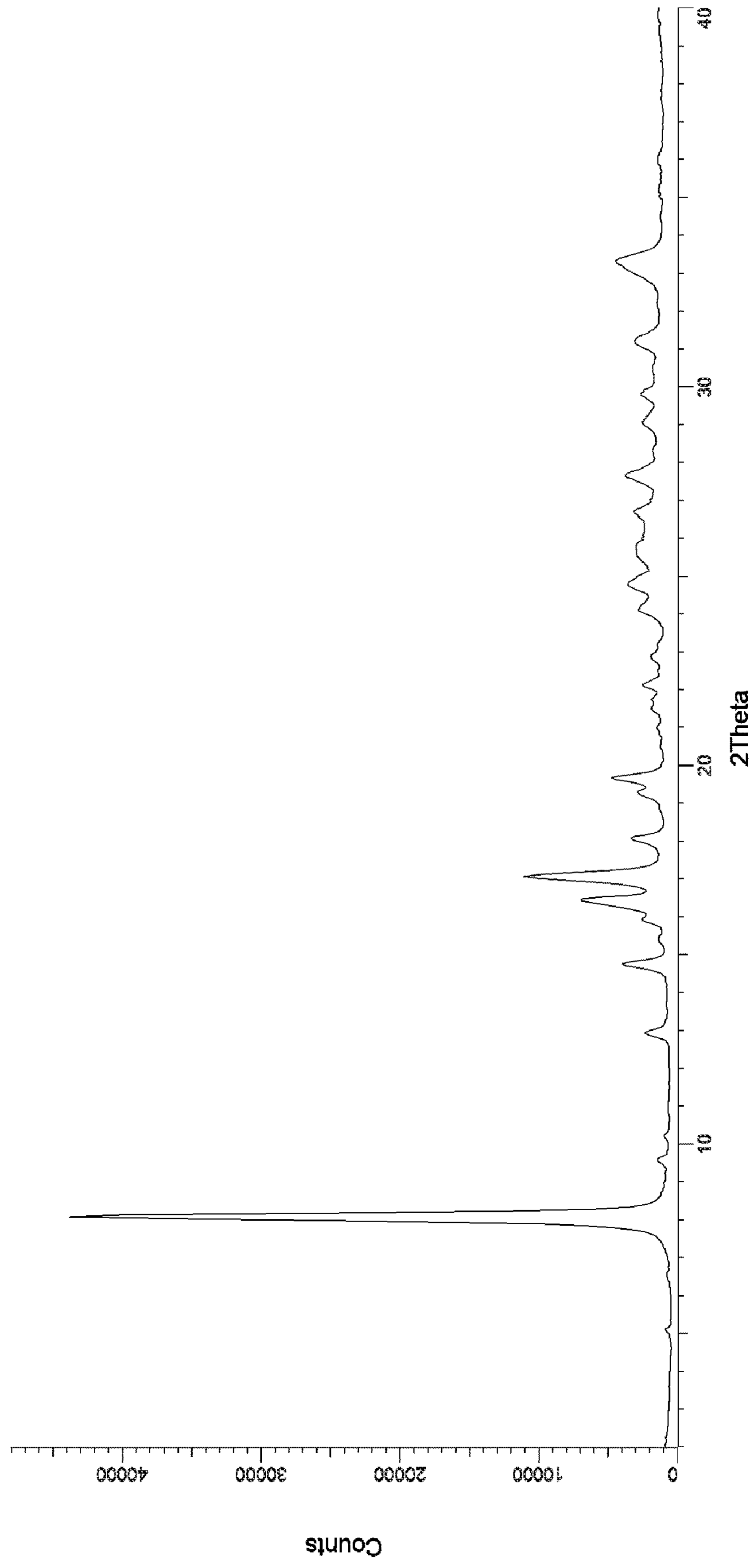

Figure 13: XRPD of Trilaciclib dihydrochloride salt Form THCl3
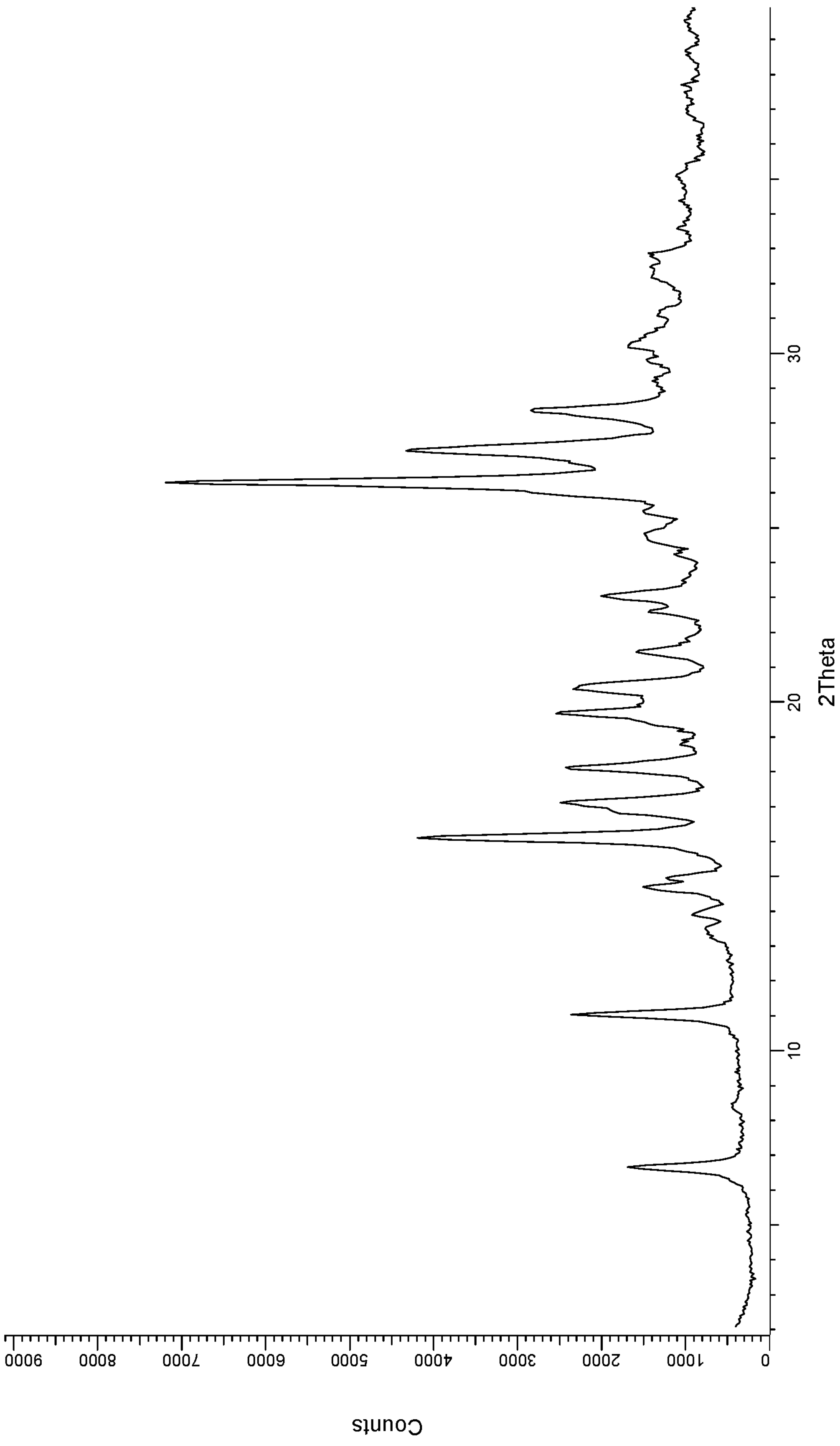

Figure 14: XRPD of Trilaciclib dihydrochloride salt Form THC14
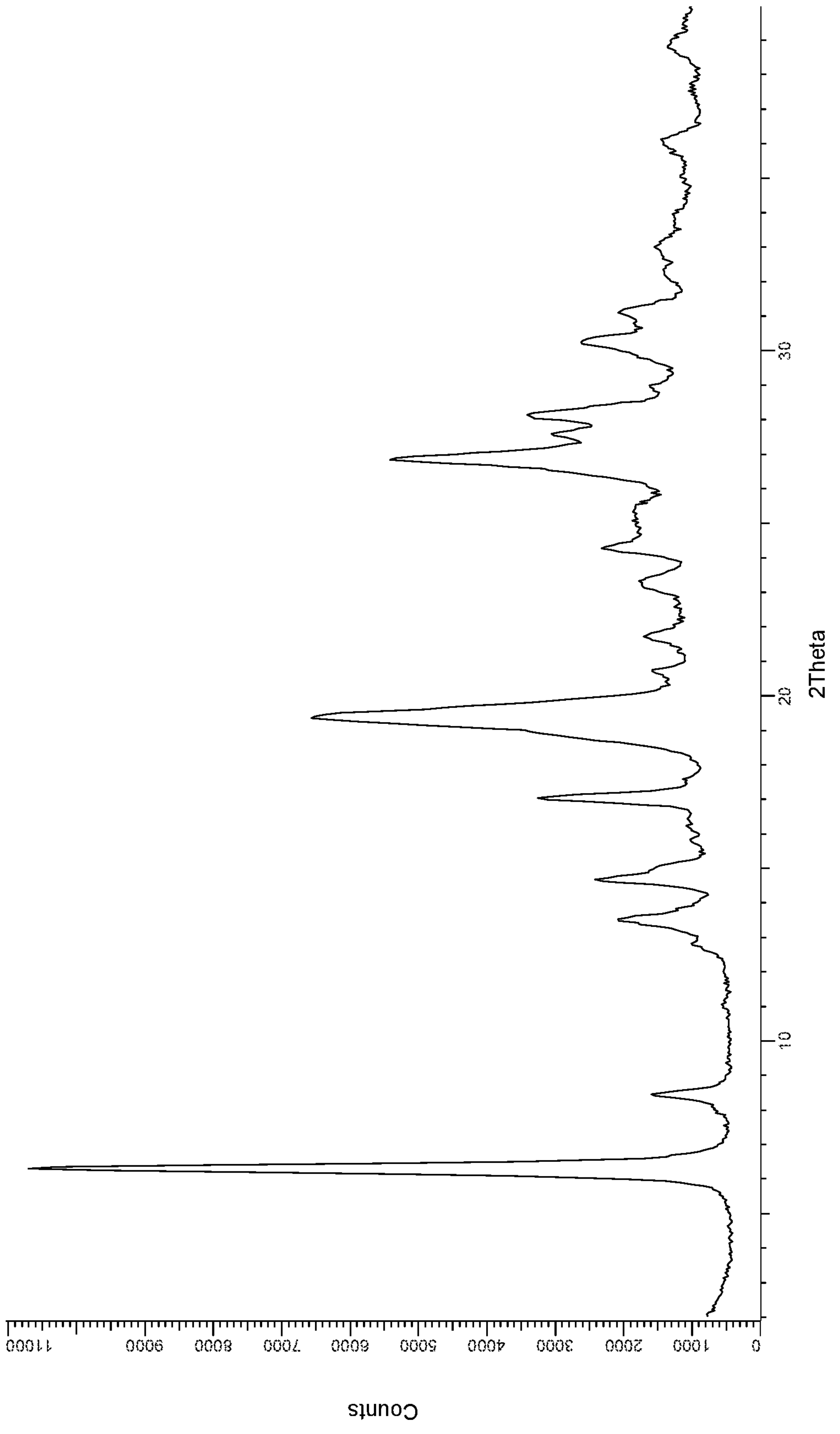

Figure 15: XRPD of Trilaciclib dihydrochloride salt Form THC15
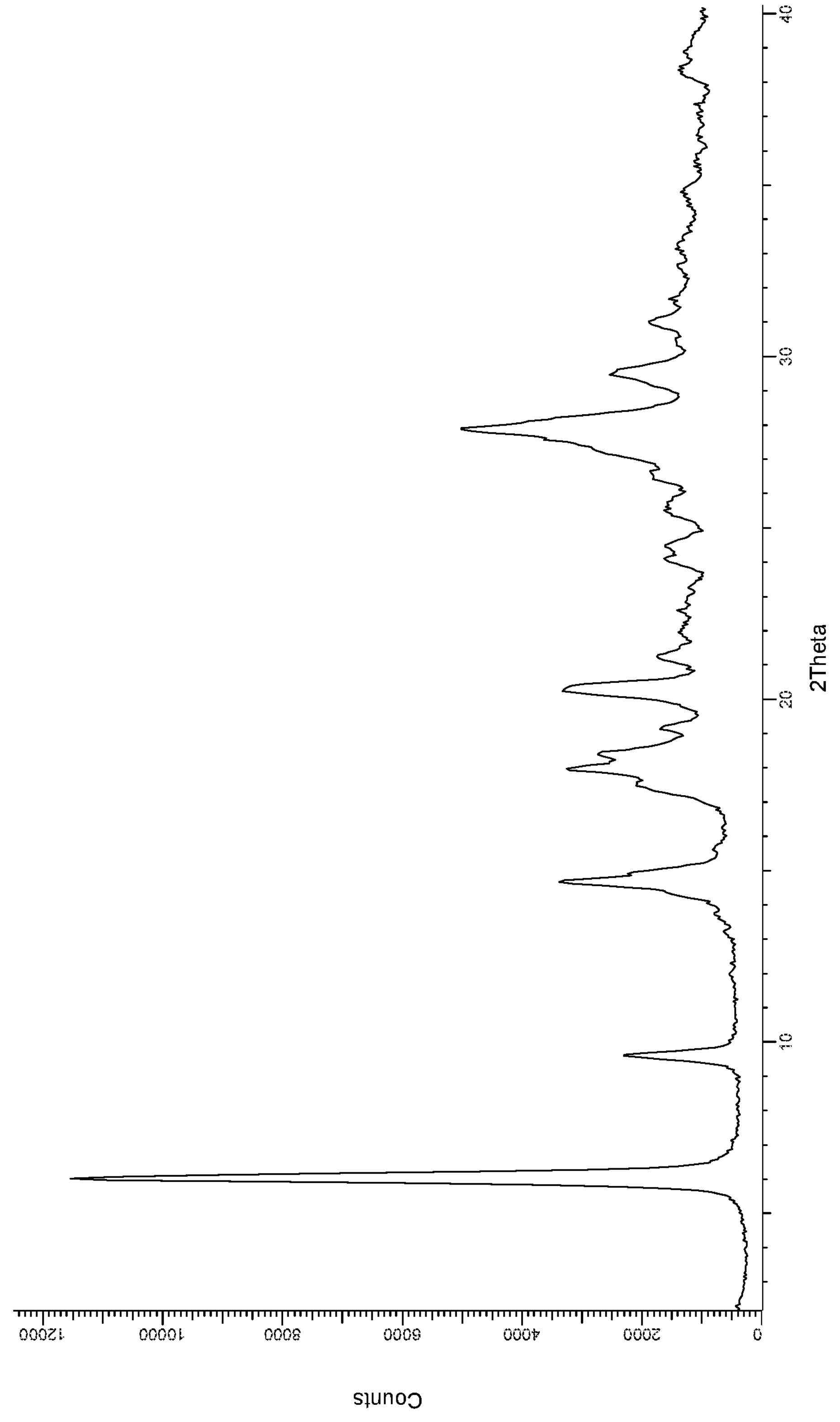

Figure 16: XRPD of Trilaciclib dihydrochloride salt Form THC16
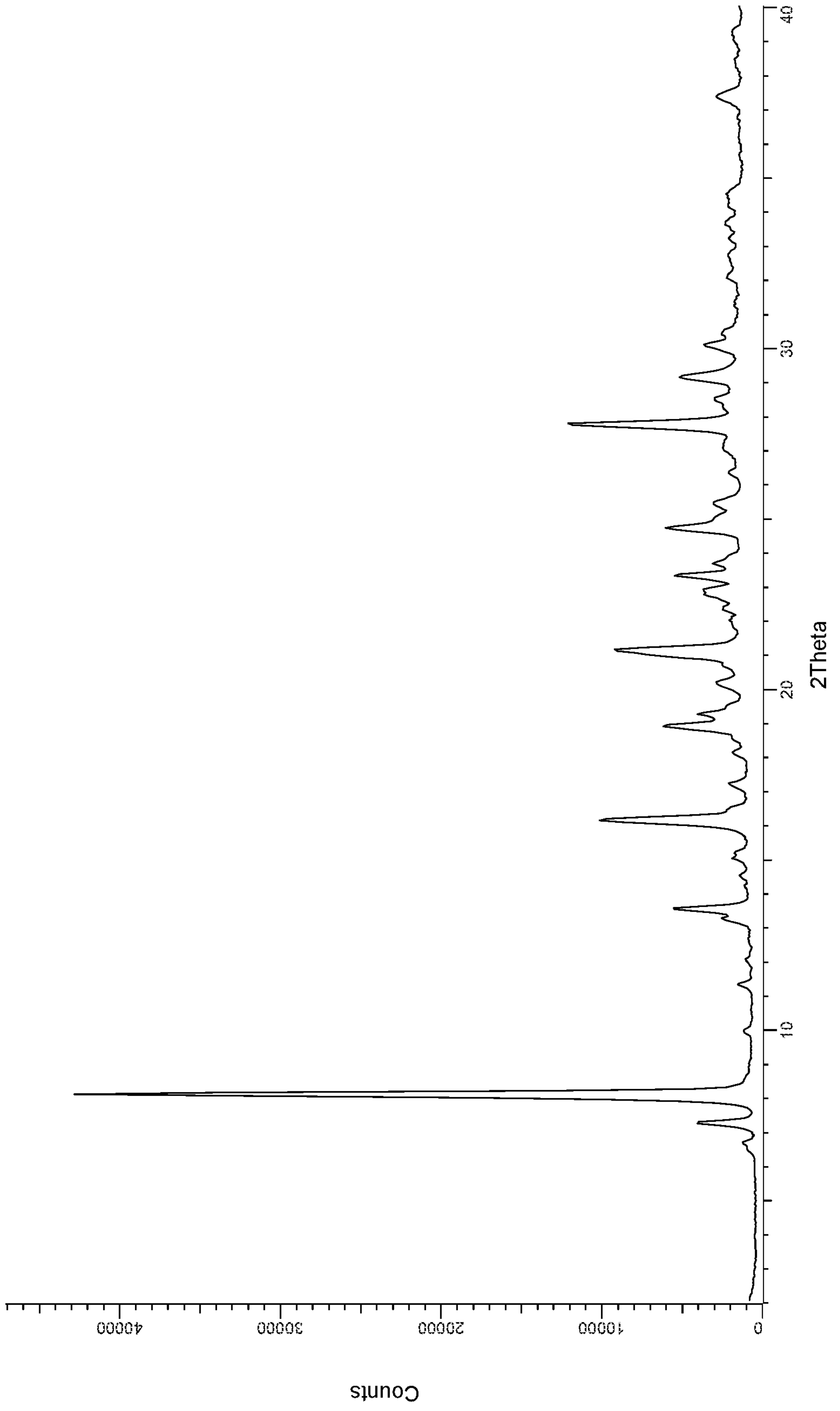

Figure 17: XRPD of Trilaciclib hydrobromide salt Form THBr1:
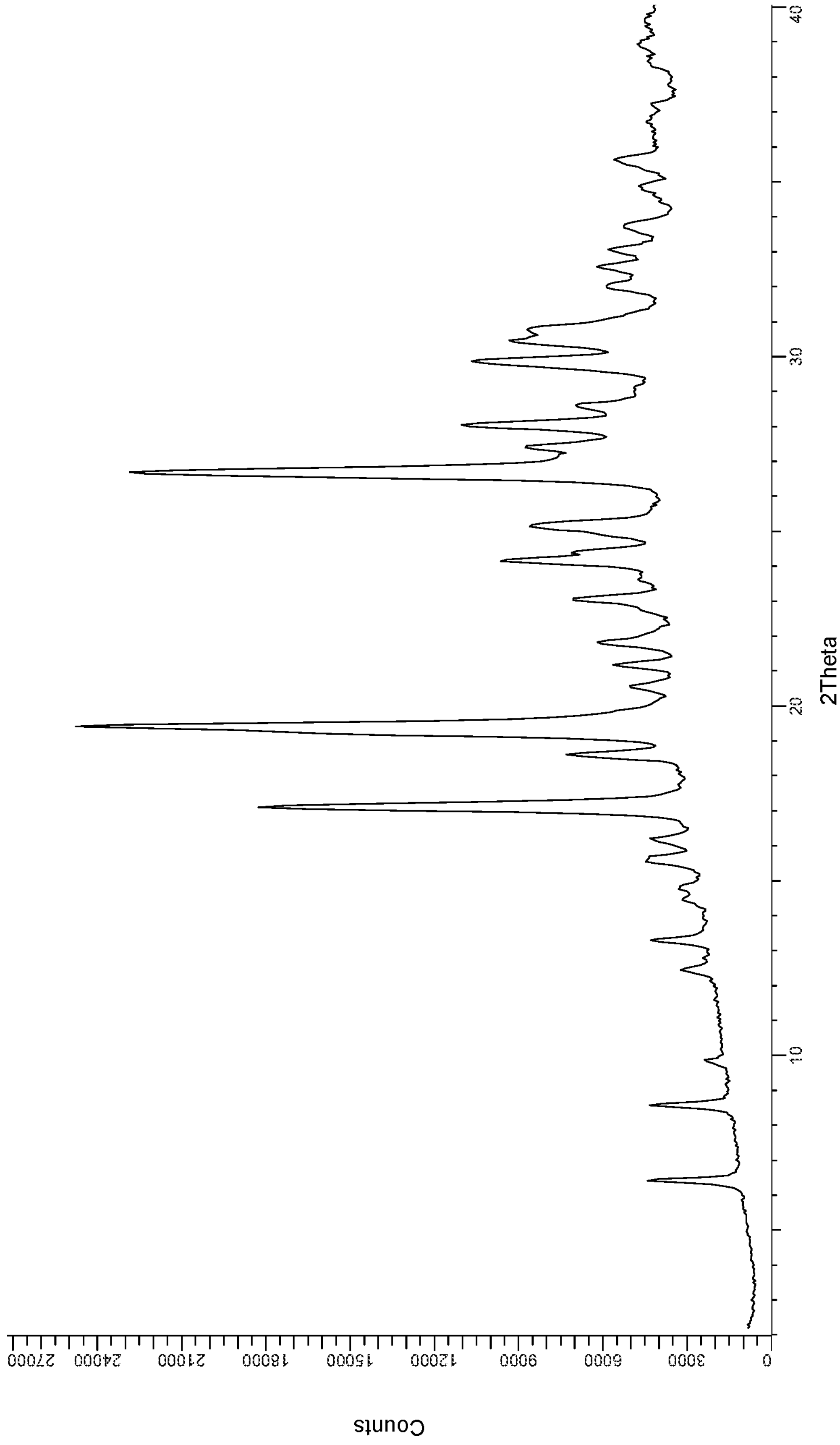

SOLID STATE FORMS OF TRILACICLIB AND OF TRILACICLIB SALTS

CROSS REFERENCE TO RELATED APPLICATIONS

This application is a National Stage of, and claims priority to and the benefit of, International Patent Application No. PCT/US2021/054110, filed Oct. 8, 2021, which, in turn, claims the benefit of and priority to, Indian Provisional Application No. 202011043937, filed on Oct. 8, 2020; Indian Provisional Application No. 202011048631, filed on Nov. 6, 2020; and Indian Provisional Application No. 202011053223, filed on Dec. 7, 2020, the entire disclosures of each of which are incorporated by reference herein.

FIELD OF THE DISCLOSURE

The present disclosure encompasses solid state forms of Trilaciclib and of Trilaciclib salts, in embodiments crystalline polymorphs of Trilaciclib and of Trilaciclib salts, processes for preparation thereof, and pharmaceutical compositions thereof.

BACKGROUND OF THE DISCLOSURE

Trilaciclib, has the following chemical structure:

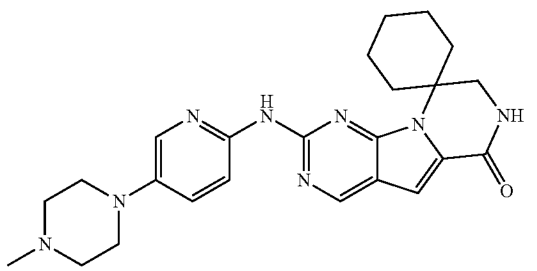 [SMILES: CN1CCN(c2ccc(Nc3ncc4cc5n(c4n3)C3(CCCCC3)CNC5=O)nc2)CC1]

Trilaciclib is a small molecule with potential antineoplastic and chemoprotective activities. In particular, it is investigated for myelopreservation (preserving bone marrow function) in patients with small cell lung cancer (SCLC) that receive chemotherapy. Trilaciclib is also under clinical investigation for myelopreservation (i.e., reducing bone marrow suppression) in patients with non-small cell lung cancer (NSCLC), colorectal cancer (particularly metastatic colorectal cancer), breast cancer (particularly metastatic triple-negative breast cancer), and bladder cancer (particularly advanced/metastatic bladder cancer), that receive chemotherapy.

The compound is described in U.S. Pat. No. 8,598,186. U.S. Pat. No. 10,988,479 describes different polymorphs of Trilaciclib and Trilaciclib DiHCl; WO2018/005865 discloses a process for preparing pyrimidine-based compounds.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Trilaciclib and of Trilaciclib salts.

SUMMARY OF THE DISCLOSURE

The present disclosure provides crystalline polymorphs of Trilaciclib, Trilaciclib salts, and solvates of Trilaciclib or Trilaciclib salts, processes for preparation thereof, and pharmaceutical compositions thereof. These crystalline polymorphs can be used to prepare other forms of Trilaciclib, Trilaciclib salts, or solvates of Trilaciclib or Trilaciclib salts.

The present disclosure provides crystalline polymorphs of Trilaciclib, Trilaciclib salts, and solvates of Trilaciclib or Trilaciclib salts, for use in the preparation of pharmaceutical compositions and/or formulations for use in medicine, in embodiments for the treatment of myelosuppression during chemotherapy, particularly for reducing chemotherapy-induced bone marrow suppression in patients with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC.

The present disclosure provides crystalline polymorphs of Trilaciclib, Trilaciclib salts, and solvates of Trilaciclib or Trilaciclib salts, for use in medicine, including as a chemoprotective agent (in particular; in patients suffering from: SCLC, colorectal cancer, breast cancer (particularly metastatic triple-negative breast cancer), and bladder cancer (particularly advanced/metastatic bladder cancer), and particularly SCLC, that receive chemotherapy), particularly for reducing chemotherapy-induced bone marrow suppression in patients with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC.

The present disclosure also encompasses the use of crystalline polymorphs of Trilaciclib, Trilaciclib salts, and solvates of Trilaciclib or Trilaciclib salts, of the present disclosure for the preparation of pharmaceutical compositions and/or formulations.

In another aspect, the present disclosure provides pharmaceutical compositions comprising any one or a combination of the crystalline polymorphs of Trilaciclib and/or Trilaciclib salts, and/or solvates of Trilaciclib or Trilaciclib salts, according to the present disclosure.

The present disclosure includes processes for preparing the above mentioned pharmaceutical compositions. The processes include combining any one or a combination of the crystalline polymorphs of Trilaciclib and/or Trilaciclib salts, and/or solvates of Trilaciclib or Trilaciclib salts, with at least one pharmaceutically acceptable excipient.

The crystalline polymorphs of Trilaciclib, Trilaciclib salts, and solvates of Trilaciclib or Trilaciclib salts, as defined herein and the pharmaceutical compositions or formulations of the crystalline polymorphs of Trilaciclib, Trilaciclib salts, and solvates of Trilaciclib or Trilaciclib salts, may be used as medicaments, such as for the treatment of myelosuppression during chemotherapy, particularly for reducing chemotherapy-induced bone marrow suppression in patients with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC.

The present disclosure also provides methods of treating myelosuppression during chemotherapy by administering a therapeutically effective amount of any one or a combination of the crystalline polymorphs of Trilaciclib and/or Trilaciclib salts, and/or solvates of Trilaciclib or Trilaciclib salts, of the present disclosure, or at least one of the above pharmaceutical compositions, to a subject suffering from myelosuppression, particularly chemotherapy-induced myelosuppression (particularly myelosuppression in a subject with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC, or otherwise in need of the treatment.

The present disclosure also provides uses of crystalline polymorphs of Trilaciclib and/or Trilaciclib salts, and/or solvates of Trilaciclib or Trilaciclib salts, of the present disclosure, or at least one of the above pharmaceutical compositions, for the manufacture of medicaments for treating, e.g., myelosuppression, particularly chemotherapy-induced myelosuppression, and particularly for reducing chemotherapy-induced bone marrow suppression in patients with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC.

In any embodiment of the present disclosure the patients or subjects may be receiving chemotherapy with any antineoplastic drug, particularly gemcitabine, docetaxel, fluorouracil, leucovorin, platinum-based chemotherapy drugs including carboplatin, and oxaliplatin, etoposide irinotecan, topotecan, or any combination of one or more thereof.

BRIEF DESCRIPTION OF THE DRAWINGS

FIG. 1 shows a characteristic X-ray powder diffraction pattern (XRPD) of Trilaciclib Form TT1.

FIG. 2 shows a characteristic XRPD of Trilaciclib Form TT2.

FIG. 3 shows a characteristic XRPD of Trilaciclib Form TT3.

FIG. 4 shows a characteristic XRPD of Trilaciclib Form TT4.

FIG. 5 shows a characteristic XRPD of Trilaciclib trifluoroacetate salt Form TTFA1.

FIG. 6 shows a characteristic XRPD of Trilaciclib dihydrochloride salt Form THCl1.

FIG. 7 shows a characteristic XRPD of Trilaciclib hydrochloride salt Form THCl.

FIG. 8 shows a characteristic XRPD of Trilaciclib citrate salt Form TCT1.

FIG. 9 shows a characteristic XRPD of Trilaciclib sulfate salt Form TS1.

FIG. 10 shows a characteristic XRPD of Trilaciclib mesylate salt Form TMSA1.

FIG. 11 shows a characteristic XRPD of Trilaciclib besylate salt Form TBSA1

FIG. 12 shows a characteristic XRPD of Trilaciclib dihydrochloride salt Form THCl2.

FIG. 13 shows a characteristic XRPD of Trilaciclib dihydrochloride salt Form THCl3.

FIG. 14 shows a characteristic XRPD of Trilaciclib dihydrochloride salt Form THCl4.

FIG. 15 shows a characteristic XRPD of Trilaciclib dihydrochloride salt Form THCl5.

FIG. 16 shows a characteristic XRPD of Trilaciclib dihydrochloride salt Form THCl6.

FIG. 17 shows a characteristic XRPD of Trilaciclib hydrobromide salt Form THBr1.

DETAILED DESCRIPTION OF THE DISCLOSURE

The present disclosure encompasses solid state forms of Trilaciclib, Trilaciclib salts, and solvates of Trilaciclib or Trilaciclib salts, processes for preparation thereof, and pharmaceutical compositions thereof.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Trilaciclib, Trilaciclib salts, or a solvate of Trilaciclib or Trilaciclib salts, described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Trilaciclib, Trilaciclib salt, or solvates of Trilaciclib or Trilaciclib salt. In some embodiments of the disclosure, the described crystalline polymorph of Trilaciclib, Trilaciclib salt, or solvate of Trilaciclib or Trilaciclib salt, may contain from about 1% to about 20% (w/w), from about 5% to about 20% (w/w), or from about 5% to about 10% (w/w) of one or more other crystalline polymorph of Trilaciclib, Trilaciclib salt, and/or solvate of Trilaciclib or Trilaciclib salt.

Depending on which other crystalline polymorphs a comparison is made, the crystalline polymorphs of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

The crystalline polymorphs of the present disclosure may, in particular, be stable to stress conditions such as: grinding, pressure, heating, and/or exposure to humidity, and may have advantageous solubility characteristics at physiologically relevant pH values.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Trilaciclib or salt of Trilaciclib referred to herein as being characterized by graphical data "as depicted in" or "as substantially depicted in" a Figure will thus be to include any crystal forms of Trilaciclib and of Trilaciclib salt characterized with the graphical data having such small variations, as are well known to the skilled person, in comparison with the Figure.

As used herein, and unless stated otherwise, the term "anhydrous" in relation to crystalline forms of Trilaciclib, relates to a crystalline form of Trilaciclib which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, unless stated otherwise, the XRPD measurements are taken using copper Kα radiation wavelength 1.5418 Å. XRPD peaks reported herein are measured using CuK α radiation, λ=1.5418 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Trilaciclib, designated TT1. The crystalline Form TT1 of Trilaciclib may be characterized by data selected from one or more of the following: an X-ray powder diffraction pattern substantially as depicted in FIG. 1; an X-ray powder diffraction pattern having peaks at 5.6, 10.7, 11.5, 17.4 and 23.1 degrees 2-theta±0.2 degrees 2-theta; and combinations of these data.

Crystalline Form TT1 of Trilaciclib may be further characterized by an X-ray powder diffraction pattern having peaks at 5.6, 10.7, 11.5, 17.4 and 23.1 degrees 2-theta±0.2 degrees 2-theta, and also having any one, two, three or four additional peaks selected from 18.5, 19.0, 21.5 and 24.4 degrees 2-theta±0.2 degrees 2-theta.

Crystalline Form TT1 of Trilaciclib may be alternatively characterized by an X-ray powder diffraction pattern having peaks at 5.6, 10.7, 11.5, 17.4, 18.5, 19.0, 21.5, 23.1, and 24.4 degrees 2-theta±0.2 degrees 2-theta.

In one embodiment of the present disclosure, crystalline Form TT1 of Trilaciclib is isolated.

Crystalline Form TT1 of Trilaciclib is anhydrous form.

In another embodiment, the present disclosure includes a crystalline polymorph of Trilaciclib, designated Form TT2. The crystalline Form TT2 of Trilaciclib may be characterized by data selected from one or more of the following: an X-ray powder diffraction pattern substantially as depicted in FIG. 2; an X-ray powder diffraction pattern having peaks at 8.1, 9.1, 11.0, 14.5 and 15.9 degrees 2-theta±0.2 degrees 2-theta; and combinations of these data.

Crystalline Form TT2 of Trilaciclib may be further characterized by an X-ray powder diffraction pattern having peaks at 8.1, 9.1, 11.0, 14.5 and 15.9 degrees 2-theta±0.2 degrees 2-theta, and also having any one, two, three or four additional peaks selected from 19.6, 20.2, 22.1 and 27.2 degrees 2-theta±0.2 degrees 2-theta.

Crystalline Form TT2 of Trilaciclib may be alternatively characterized by an X-ray powder diffraction pattern having peaks at 8.1, 9.1, 11.0, 14.5, 15.9, 19.6, 20.2, 22.1, and 27.degrees 2-theta±0.2 degrees 2-theta.

In one embodiment of the present disclosure, crystalline Form TT2 of Trilaciclib is isolated.

Crystalline Form TT2 of Trilaciclib is acetic acid solvate. Alternatively, crystalline Form TT2 is a salt of Trilaciclib with acetic acid (i.e., Trilaciclib acetate salt).

In another embodiment, the present disclosure includes a crystalline polymorph of Trilaciclib, designated Form TT3. The crystalline Form TT3 of Trilaciclib may be characterized by data selected from one or more of the following: an X-ray powder diffraction pattern substantially as depicted in FIG. 3; an X-ray powder diffraction pattern having peaks at 5.3, 10.2, 10.8, 17.8 and 25.2 degrees 2-theta±0.2 degrees 2-theta; and combinations of these data.

Crystalline Form TT3 of Trilaciclib may be further characterized by an X-ray powder diffraction pattern having peaks at 5.3, 10.2, 10.8, 17.8 and 25.2 degrees 2-theta±0.2 degrees 2-theta, and also having any one, two, three or four additional peaks selected from 15.3, 18.6, 23.6 and 24.0 degrees 2-theta±0.2 degrees 2-theta.

Crystalline Form TT3 of Trilaciclib may be alternatively characterized by an X-ray powder diffraction pattern having peaks at 5.3, 10.2, 10.8, 15.3, 17.8, 18.6, 23.6, 24.0, and 25.2 degrees 2-theta±0.2 degrees 2-theta.

In one embodiment of the present disclosure, crystalline Form TT3 of Trilaciclib is isolated.

Crystalline Form TT3 of Trilaciclib is formic acid solvate. Alternatively, crystalline Form TT3 is a salt of Trilaciclib with formic acid (i.e., Trilaciclib formic salt). The molar ratio between Trilaciclib and formic acid may be 1:2.

In a further embodiment, the present application discloses a crystalline polymorph of Trilaciclib, designated Form TT4. The crystalline Form TT4 of Trilaciclib may be characterized by data selected from one or more of the following: an X-ray powder diffraction pattern substantially as depicted in FIG. 4; an X-ray powder diffraction pattern having peaks at 13.1, 18.1, 19.1, 20.9 and 23.3 degrees 2-theta±0.2 degrees 2-theta; and combinations of these data.

Crystalline Form TT4 of Trilaciclib may be further characterized by an X-ray powder diffraction pattern having peaks at 13.1, 18.1, 19.1, 20.9 and 23.3 degrees 2-theta±0.2 degrees 2-theta, and also having any one, two, three or four additional peaks selected from 7.1, 9.7, 22.4 and 27.4 degrees 2-theta±0.2 degrees 2-theta.

Crystalline Form TT4 of Trilaciclib may be alternatively characterized by an X-ray powder diffraction pattern having peaks at 7.1, 9.7, 13.1, 18.1, 19.1, 20.9, 22.4, 23.3, and 27.4 degrees 2-theta±0.2 degrees 2-theta.

In one embodiment of the present disclosure, crystalline Form TT4 of Trilaciclib is isolated.

Crystalline Form TT4 of Trilaciclib is propionic acid solvate. Alternatively, crystalline Form TT4 is a salt of Trilaciclib with propionic acid (i.e., Trilaciclib propionate salt).

In a further embodiment, the present disclosure includes a crystalline polymorph of Trilaciclib trifluoroacetate salt; designated Form TTFA1. The crystalline Form TTFA1 may be characterized by data selected from one or more of the following: an X-ray powder diffraction pattern substantially as depicted in FIG. 5; an X-ray powder diffraction pattern having peaks at 5.8, 16.2, 17.7, 18.4 and 26.7 degrees 2-theta±0.2 degrees 2-theta; and combinations of these data.

Crystalline Form TTFA1 of Trilaciclib trifluoroacetic acid salt may be further characterized by an X-ray powder diffraction pattern having peaks at 5.8, 16.2, 17.7, 18.4 and 26.7 degrees 2-theta±0.2 degrees 2-theta, and also having any one, two, three or four additional peaks selected from 8.9, 14.1, 26.0 and 36.0 degrees 2-theta±0.2 degrees 2-theta.

Crystalline Form TTFA1 of Trilaciclib trifluoroacetic acid salt may be alternatively characterized by an X-ray powder diffraction pattern having peaks at 5.8, 8.9, 14.1, 16.2, 17.7, 18.4, 26.0, 26.7, and 36.0 degrees 2-theta±0.2 degrees 2-theta.

An aspect of the present disclosure provides a Trilaciclib hydrochloride salt, for example Trilaciclib monohydrochloride or Trilaciclib dihydrochloride. Advantageously, Trilaciclib monohydrochloride or Trilaciclib dihydrochloride may be crystalline.

A further aspect of the present disclosure therefore provides, e.g., crystalline Trilaciclib dihydrochloride.

A further aspect of the present disclosure provides crystalline polymorphs of Trilaciclib dihydrochloride, which may be distinguished by X-ray powder diffraction patterns having characteristic peaks.

The present disclosure further includes a crystalline polymorph of Trilaciclib dihydrochloride salt; designated Form THCl1. The crystalline Form THCl1 may be characterized by data selected from one or more of the following: an X-ray powder diffraction pattern substantially as depicted in FIG. 6; an X-ray powder diffraction pattern having peaks at 8.3, 9.4, 12.0, 19.1 and 21.1 degrees 2-theta±0.2 degrees 2-theta; and combinations of these data.

Crystalline Form THCl1 of Trilaciclib dihydrochloride salt may be further characterized by an X-ray powder diffraction pattern having peaks at 8.3, 9.4, 12.0, 19.1 and 21.1 degrees 2-theta±0.2 degrees 2-theta, and also having any one, two, three or four additional peaks selected from 4.1, 10.0, 12.6 and 23.8 degrees 2-theta±0.2 degrees 2-theta.

Crystalline Form THCl1 of Trilaciclib dihydrochloride salt may be alternatively characterized by an X-ray powder diffraction pattern having peaks at 4.1, 8.3, 9.4, 10.0, 12.0, 12.6, 19.1, 21.1, and 23.8 degrees 2-theta±0.2 degrees 2-theta.

In a further embodiment, the present disclosure includes a crystalline polymorph of Trilaciclib hydrochloride salt; designated Form THCl. The crystalline Form THCl may be characterized by data selected from one or more of the following: an X-ray powder diffraction pattern substantially as depicted in FIG. 7; an X-ray powder diffraction pattern having peaks at 6.2, 8.5, 13.6, 14.1 and 21.7 degrees 2-theta±0.2 degrees 2-theta; and combinations of these data.

Crystalline Form THCl of Trilaciclib hydrochloride salt may be further characterized by an X-ray powder diffraction pattern having peaks at 6.2, 8.5, 13.6, 14.1 and 21.7 degrees 2-theta±0.2 degrees 2-theta, and also having any one, two, three or four additional peaks selected from 12.3, 17.9, 18.7 and 19.4 degrees 2-theta±0.2 degrees 2-theta.

Crystalline Form THCl of Trilaciclib hydrochloride salt may be alternatively characterized by an X-ray powder diffraction pattern having peaks at 6.2, 8.5, 12.3, 13.6, 14.1, 17.9, 18.7, 19.4, and 21.7 degrees 2-theta±0.2 degrees 2-theta.

In a further embodiment, the present disclosure includes a crystalline polymorph of Trilaciclib citrate salt; designated Form TCT1. The crystalline Form TCT1 may be characterized by data selected from one or more of the following: an X-ray powder diffraction pattern substantially as depicted in FIG. 8; an X-ray powder diffraction pattern having peaks at 6.1, 7.3, 11.3, 15.3 and 19.3 degrees 2-theta±0.2 degrees 2-theta; and combinations of these data.

Crystalline Form TCT1 of Trilaciclib citrate salt may be further characterized by an X-ray powder diffraction pattern having peaks at 6.1, 7.3, 11.3, 15.3 and 19.3 degrees 2-theta±0.2 degrees 2-theta, and also having any one, two, three or four additional peaks selected from 8.9, 9.3, 20.4 and 22.7 degrees 2-theta±0.2 degrees 2-theta.

Crystalline Form TCT1 of Trilaciclib citrate salt may be alternatively characterized by an X-ray powder diffraction pattern having peaks at 6.1, 7.3, 8.9, 9.3, 11.3, 15.3, 19.3, 20.4, and 22.7 degrees 2-theta±0.2 degrees 2-theta.

In one embodiment, the present disclosure comprises a crystalline polymorph of Trilaciclib sulphate salt; designated Form TS1. The crystalline Form TS1 may be characterized by data selected from one or more of the following: an X-ray powder diffraction pattern substantially as depicted in FIG. 9; an X-ray powder diffraction pattern having peaks at 10.9, 13.5, 17.0, 20.1 and 25.2 degrees 2-theta±0.2 degrees 2-theta; and combinations of these data.

Crystalline Form TS1 of Trilaciclib sulphate salt may be further characterized by an X-ray powder diffraction pattern having peaks at 10.9, 13.5, 17.0, 20.1 and 25.2 degrees 2-theta±0.2 degrees 2-theta, and also having any one, two, three or four additional peaks selected from 6.6, 8.2, 18.2 and 18.6 degrees 2-theta±0.2 degrees 2-theta.

Crystalline Form TS1 of Trilaciclib sulphate salt may be alternatively characterized by an X-ray powder diffraction pattern having peaks at 6.6, 8.2, 10.9, 13.5, 17.0, 18.2, 18.6, 20.1, and 25.2 degrees 2-theta±0.2 degrees 2-theta.

In another embodiment, the present disclosure comprises a crystalline polymorph of Trilaciclib mesylate salt; designated Form TMSA1. The crystalline Form TMSA1 may be characterized by data selected from one or more of the following: an X-ray powder diffraction pattern substantially as depicted in FIG. 10; an X-ray powder diffraction pattern having peaks at 13.6, 15.8, 23.1, 25.1 and 28.2 degrees 2-theta±0.2 degrees 2-theta; and combinations of these data.

Crystalline Form TMSA1 of Trilaciclib mesylate salt may be further characterized by an X-ray powder diffraction pattern having peaks at 13.6, 15.8, 23.1, 25.1 and 28.2 degrees 2-theta±0.2 degrees 2-theta, and also having any one, two, three or four additional peaks selected from 6.0, 17.6, 18.2 and 22.4 degrees 2-theta±0.2 degrees 2-theta.

Crystalline Form TMSA1 of Trilaciclib mesylate salt may be alternatively characterized by an X-ray powder diffraction pattern having peaks at 6.0, 13.6, 15.8, 17.6, 18.2, 22.4, 23.1, 25.1, and 28.2 degrees 2-theta±0.2 degrees 2-theta.

In a further embodiment, the present disclosure includes a crystalline polymorph of Trilaciclib besylate salt; designated Form TBSA1. The crystalline Form TBSA1 may be characterized by data selected from one or more of the following: an X-ray powder diffraction pattern substantially as depicted in FIG. 11; an X-ray powder diffraction pattern having peaks at 9.1, 11.5, 13.4, 19.4 and 22.8 degrees 2-theta±0.2 degrees 2-theta; and combinations of these data.

Crystalline Form TBSA1 of Trilaciclib besylate salt may be further characterized by an X-ray powder diffraction pattern having peaks at 9.1, 11.5, 13.4, 19.4 and 22.8 degrees 2-theta±0.2 degrees 2-theta, and also having any one, two, three or four additional peaks selected from 18.1, 18.4, 20.4 and 23.9 degrees 2-theta±0.2 degrees 2-theta.

Crystalline Form TBSA1 of Trilaciclib besylate salt may be alternatively characterized by an X-ray powder diffraction pattern having peaks at 9.1, 11.5, 13.4, 18.1, 18.4, 19.4, 20.4, 22.8, and 23.9 degrees 2-theta±0.2 degrees 2-theta.

The present disclosure further includes a crystalline polymorph of Trilaciclib dihydrochloride salt; designated Form THCl2. The crystalline Form THCl2 may be characterized by data selected from one or more of the following: an X-ray powder diffraction pattern substantially as depicted in FIG. 12; an X-ray powder diffraction pattern having peaks at 12.9, 16.3, 19.6, 27.6 and 33.2 degrees 2-theta±0.2 degrees 2-theta; and combinations of these data.

Crystalline Form THCl2 of Trilaciclib dihydrochloride salt may be further characterized by an X-ray powder diffraction pattern having peaks at 12.9, 16.3, 19.6, 27.6 and 33.2 degrees 2-theta±0.2 degrees 2-theta, and also having any one, two, three or four additional peaks selected from 8.0, 14.6, 17.0 and 18.0 degrees 2-theta±0.2 degrees 2-theta.

Crystalline Form THCl2 of Trilaciclib dihydrochloride salt may be alternatively characterized by an X-ray powder diffraction pattern having peaks at 8.0, 12.9, 14.6, 16.3, 17.0, 18.0, 19.6, 27.6, and 33.2 degrees 2-theta±0.2 degrees 2-theta.

The present disclosure also includes a crystalline polymorph of Trilaciclib dihydrochloride salt; designated Form THCl3. The crystalline Form THCl3 may be characterized by data selected from one or more of the following: an X-ray powder diffraction pattern substantially as depicted in FIG. 13; an X-ray powder diffraction pattern having peaks at 6.6, 11.0, 16.1, 26.3 and 27.2 degrees 2-theta±0.2 degrees 2-theta; and combinations of these data.

Crystalline Form THCl3 of Trilaciclib dihydrochloride salt may be further characterized by an X-ray powder diffraction pattern having peaks at 6.6, 11.0, 16.1, 26.3 and 27.2 degrees 2-theta±0.2 degrees 2-theta, and also having any one, two, three or four additional peaks selected from 18.1, 20.5, 23.0 and 28.3 degrees 2-theta±0.2 degrees 2-theta.

Crystalline Form THCl3 of Trilaciclib dihydrochloride salt may be alternatively characterized by an X-ray powder diffraction pattern having peaks at 6.6, 11.0, 16.1, 18.1, 20.5, 23.0, 26.3, 27.2, and 28.3 degrees 2-theta±0.2 degrees 2-theta.

In another embodiment, the present disclosure includes a crystalline polymorph of Trilaciclib dihydrochloride salt; designated Form THCl4. The crystalline Form THCl4 may be characterized by data selected from one or more of the following: an X-ray powder diffraction pattern substantially as depicted in FIG. 14; an X-ray powder diffraction pattern having peaks at 6.3, 8.5, 13.5, 19.4 and 26.9 degrees 2-theta±0.2 degrees 2-theta; and combinations of these data.

Crystalline Form THCl4 of Trilaciclib dihydrochloride salt may be further characterized by an X-ray powder diffraction pattern having peaks at 6.3, 8.5, 13.5, 19.4 and 26.9 degrees 2-theta±0.2 degrees 2-theta, and also having any one, two, three or four additional peaks selected from 14.7, 17.1, 27.6 and 28.2 degrees 2-theta±0.2 degrees 2-theta.

Crystalline Form THCl4 of Trilaciclib dihydrochloride salt may be alternatively characterized by an X-ray powder diffraction pattern having peaks at 6.3, 8.5, 13.5, 14.7, 17.1, 19.4, 26.9, 27.6 and 28.2 degrees 2-theta±0.2 degrees 2-theta.

The present disclosure also includes a crystalline polymorph of Trilaciclib dihydrochloride salt; designated Form THCl5. The crystalline Form THCl5 may be characterized by data selected from one or more of the following: an X-ray powder diffraction pattern substantially as depicted in FIG. 15; an X-ray powder diffraction pattern having peaks at 6.1, 9.6, 14.7, 18.4 and 27.9 degrees 2-theta±0.2 degrees 2-theta; and combinations of these data.

Crystalline Form THCl5 of Trilaciclib dihydrochloride salt may be further characterized by an X-ray powder diffraction pattern having peaks at 6.1, 9.6, 14.7, 18.4 and 27.9 degrees 2-theta±0.2 degrees 2-theta, and also having any one, two or three additional peaks selected from 18.0, 20.3 and 29.5 degrees 2-theta±0.2 degrees 2-theta.

Crystalline Form THCl5 of Trilaciclib dihydrochloride salt may be alternatively characterized by an X-ray powder diffraction pattern having peaks at 6.1, 9.6, 14.7, 18.0, 18.4, 20.3, 27.9, and 29.5 degrees 2-theta±0.2 degrees 2-theta.

The present disclosure further comprises a crystalline polymorph of Trilaciclib dihydrochloride salt; designated Form THCl6. The crystalline Form THCl6 may be characterized by data selected from one or more of the following: an X-ray powder diffraction pattern substantially as depicted in FIG. 16; an X-ray powder diffraction pattern having peaks at 7.3, 18.9, 23.3, 27.7 and 29.2 degrees 2-theta±0.2 degrees 2-theta; and combinations of these data.

Crystalline Form THCl6 of Trilaciclib dihydrochloride salt may be further characterized by an X-ray powder diffraction pattern having peaks at 7.3, 18.9, 23.3, 27.7 and 29.2 degrees 2-theta±0.2 degrees 2-theta, and also having any one, two, three or four additional peaks selected from 8.1, 13.5, 16.2 and 21.1 degrees 2-theta±0.2 degrees 2-theta.

Crystalline Form THCl6 of Trilaciclib dihydrochloride salt may be alternatively characterized by an X-ray powder diffraction pattern having peaks at 7.3, 8.1, 13.5, 16.2, 18.9, 21.1, 23.3, 27.7 and 29.2 degrees 2-theta±0.2 degrees 2-theta.

Crystalline Form THCl6 of Trilaciclib dihydrochloride salt may be prepared by combining a solution of Trilaciclib dihydrochloride in a solvent with an antisolvent. The solvent may be selected from alcohols, water, and mixtures thereof.

Preferably, the solvent is a mixture of alcohols (preferably a $C_1$ to $C_4$ alcohol, and more particularly methanol) and water. In any embodiment of the process, the ratio of alcohol:water, preferably methanol:water is from: about 4:1 to about 1:4, about 3.5:1 to about 1:3.5, about 3:1 to about 3:1 to about 1:3; about 2.5:1 to about 1:1.5, about 2.4:1 to about 1:1, or about 2.4:1 to about 2.3:1

The antisolvent may be an ether, an ester or an alkane. The ether may be a $C_{4-8}$ ether, and more preferably methyl tert-butyl ether (MTBE) or diisopropyl ether. The alkane may be $C_{5-8}$ straight or branched alkane, and more preferably heptane or hexane. The ester may be C2-5 ester; preferably ethyl acetate. In any embodiment of the process the antisolvent may be an ether, particularly a $C_{4-8}$ ether, and more particularly methyl tert-butyl ether.

The antisolvent may be added to the solution, or the solution may be added to the antisolvent (reverse addition). Preferably, the solution is added to the antisolvent. In any embodiment, the antisolvent may be pre-cooled prior to combining with the solution. In any embodiment, the solution may be added slowly to the antisolvent, for example, the solvent may be added dropwise to the antisolvent. Particularly, the solvent may be added dropwise to a precooled antisolvent. The pre-cooled antisolvent may be at a temperature of: about −5° C. to about 15° C., about −2° C. to about 10° C., or about 0° C. to about 5° C. Optionally, the mixture is stirred during the addition.

In any embodiment the antisolvent:solvent ratio (v/v) may be: about 15:1 to about 1:5, about 10:1 to about 1:5, about 8:1 to about 1:2, about 5:1 to about 1:1, about 4:1 to about 2:1, about 3.5:1 to about 3:1 or about 3:1.

Following combining the solution with the antisolvent, the mixture may be stirred, optionally with cooling. Preferably, the cooling is to: about −5° C. to about 15° C., about −2° C. to about 10° C., or about 0° C. to about 5° C. The stirring may be for any suitable period of time, optionally for about 0.5 hours to about 10 hours, about 0.7 hours to about 8 hours, about 1 hour to about 6 hours, or about 2 hours to about 4 hours.

In any embodiment of the process, the process may further comprise isolating the Trilaciclib dihydrochloride Form THCl6 by any suitable procedure, such as centrifugation, decantation, or filtration, optionally filtration. Following isolation, the product may be dried. Preferably the drying is under reduced pressure. The drying may be carried out at elevated temperature, for example a temperature of: about 30° C. to about 120° C., about 40° C. to about 100° C., about 50° C. to about 80° C., about 50° C. to about 70° C., about 55° C. to about 65° C., or about 60° C. The drying may be for any suitable period of time, for example, about 6 hours to about 48 hours, about 10 hours to about 40 hours, about 18 to about 30 hours, about 20 to about 28 hours, or about 24 hours.

In another embodiment, crystalline form THCl6 of Trilaciclib dihydrochloride salt can be prepared by stirring Trilaciclib dihydrochloride in an organic solvent (preferably wherein the organic solvent is, or comprises, a mixture of acetonitrile and an alcohol, more particularly wherein the alcohol is a $C_{1-6}$ alcohol, particularly methanol, ethanol or isopropanol, and especially isopropanol. The vol/vol ratio of acetonitrile to alcohol (preferably isopropanol) may be: about 200:1 to about 10:1, about 180:1 to about 50:1, about 150:1 to about 60:1, about 120:1 to about 80:1, about 110:1 to about 90:1, or about 100:1. The mixture may be stirred at a temperature of: about −5° C. to about 15° C., about −2° C. to about 10° C., or about 0° C. to about 5° C. The stirring may be for any suitable period of time to prepare Form THCl6 of Trilaciclib dihydrochloride salt. Particularly, the stirring may be for a period of time of: about 6 hours to about 48 hours, about 10 hours to about 40 hours, about 15 hours to about 30 hours, about 18 hours to about 24 hours, or about 20 hours. In any embodiment of this process, mixture of Trilaciclib dihydrochloride in a solvent comprising acetonitrile and an alcohol as described above, may be prepared by combining Trilaciclib in a solution with acetonitrile, with a solution of hydrochloric acid in the alcohol (preferably isopropanol). According to any embodiment of this process, the hydrochloric acid is in the form of hydrogen chloride in alcohol solvent, more particularly a $C_{1-6}$ alcohol, and especially isopropanol. Preferably, the hydrochloric acid is added to the Trilaciclib solution. Following the addition, the mixture may be stirred as described above. In any embodiment of the process, the process may further comprise isolating the Trilaciclib dihydrochloride Form THCl6 by any suitable procedure, such as centrifugation, decantation, or filtration, optionally filtration. Following isolation, the product may be dried. Preferably the drying is under reduced pressure. The drying may be carried out at elevated temperature, for example a temperature of: about 18° C. to about 50° C., about 20° C. to about 40° C., about 22° C. to about 30° C., or about 25° C. The drying may be for any suitable period of time, for example, about 2 to about 60 minutes, about 5 to about 30 minutes, about 10 to about 15 minutes.

Yet in another embodiment, the present disclosure includes a crystalline polymorph of Trilaciclib hydrobromide salt; designated Form THBr1. The crystalline Form THBr1 may be characterized by data selected from one or more of the following: an X-ray powder diffraction pattern substantially as depicted in FIG. 17; an X-ray powder diffraction pattern having peaks at 6.5, 8.6, 17.2, 19.5 and 26.8 degrees 2-theta±0.2 degrees 2-theta; and combinations of these data.

Crystalline Form THBr1 of Trilaciclib hydrobromide salt may be further characterized by an X-ray powder diffraction pattern having peaks at 6.5, 8.6, 17.2, 19.5 and 26.8 degrees 2-theta±0.2 degrees 2-theta, and also having any one, two, three or four additional peaks selected from 18.7, 25.2, 28.1 and 29.9 degrees 2-theta±0.2 degrees 2-theta.

Crystalline Form THBr1 of Trilaciclib hydrobromide salt may be further characterized by an X-ray powder diffraction pattern having peaks at 6.5, 8.6, 17.2, 18.7, 19.5, 25.2, 26.8, 28.1, and 29.9 degrees 2-theta±0.2 degrees 2-theta.

In any aspect or embodiment of the present disclosure, any of the solid state forms of Trilaciclib, Trilaciclib salts, or solvates of Trilaciclib or Trilaciclib salts, described herein may be polymorphically pure or may be substantially free of any other solid state forms of the subject Trilaciclib, Trilaciclib salts, or solvates of Trilaciclib or Trilaciclib salts (for example a crystalline Trilaciclib which is polymorphically pure, may be substantially free of any other solid state forms of Trilaciclib; a crystalline Trilaciclib salt which is polymorphically pure, may be substantially free of any other solid state form of the Trilaciclib salt). In any aspect or embodiment of the present disclosure, any of the solid state forms of Trilaciclib, Trilaciclib salts, or solvates of Trilaciclib or Trilaciclib salts, described in any aspect or embodiment disclosed herein, may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound (i.e. Trilaciclib, Trilaciclib salts, or solvates of Trilaciclib or Trilaciclib salts, respectively), preferably as measured by XRPD. Thus, any of the disclosed crystalline forms of Trilaciclib, Trilaciclib salts, or solvates of Trilaciclib or Trilaciclib salts, described herein may be substantially free of any other solid state forms of the subject Trilaciclib, Trilaciclib salts, or solvates of Trilaciclib or Trilaciclib salts, respectively, and may contain greater than about 80% (w/w), greater than about 90% (w/w), greater than about 95% (w/w), greater than about 98% (w/w), greater than about 99% (w/w), or about 100% of the subject solid state form of the Trilaciclib, Trilaciclib salts, or solvates of Trilaciclib or Trilaciclib salts, respectively.

The above crystalline polymorphs of Trilaciclib and of Trilaciclib salts can be used to prepare other crystalline polymorphs of Trilaciclib, other Trilaciclib salts, solvates of Trilaciclib or Trilaciclib salts, and solid state forms thereof.

In any aspect or embodiment of the present disclosure, the crystalline form may be in the form of a solvate, or a hydrate, or a mixed solvate-hydrate. In embodiments, for example, a Trilaciclib hydrochloride as described in any aspect of the present disclosure, may be in the form of a hydrate, i.e., the disclosure encompasses Trilaciclib hydrochlorides, such as Trilaciclib dihydrochloride, or the specific Trilaciclib hydrochlorides denoted herein as THCl1-THCl6, may be in the form of a hydrate. The hydrate may be a hemi-, mono-, di-, tri-, tetra-, penta-, or hexa-hydrate. In aspects, higher hydrates (e.g., tri-, tetra-, penta-, or hexa-) may be preferred. For example, in any aspect or embodiment of the present disclosure, as described herein, including crystalline Trilaciclib dihydrochloride, or the specific crystalline forms of Trilaciclib dihydrochloride denoted herein as THCl1-THCl6, may be in the form of a hydrate, including a pentahydrate.

The present disclosure provides crystalline polymorphs of Trilaciclib, Trilaciclib salts, and solvates of Trilaciclib or Trilaciclib salts, for use in the preparation of pharmaceutical compositions including Trilaciclib, Trilaciclib salts, and solvates of Trilaciclib or Trilaciclib salts and/or crystalline polymorphs thereof.

The present disclosure also encompasses the use of crystalline polymorphs of Trilaciclib, Trilaciclib salts, and solvates of Trilaciclib or Trilaciclib salts, of the present disclosure for the preparation of pharmaceutical compositions of crystalline polymorphs Trilaciclib, Trilaciclib salts, and solvates of Trilaciclib or Trilaciclib salts, and/or crystalline polymorphs thereof.

The present disclosure includes processes for preparing the above-mentioned pharmaceutical compositions. The processes include combining any one or a combination of the crystalline polymorphs of Trilaciclib and/or Trilaciclib salts, and/or solvates of Trilaciclib or Trilaciclib salts, of the present disclosure with at least one pharmaceutically acceptable excipient.

Pharmaceutical combinations or formulations of the present disclosure contain any one or a combination of the solid state forms of Trilaciclib, Trilaciclib salts, and solvates of Trilaciclib or Trilaciclib salts, of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Trilaciclib and Trilacicilib salt, and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Trilaciclib or of Trilaciclib salt can be administered. Trilaciclib, Trilaciclib salt, and solvates of Trilaciclib or Trilaciclib salts, may be formulated for administration to a mammal, in embodiments to a human, by injection. Trilaciclib or Trilaciclib salt can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Trilaciclib and of Trilaciclib salts, and the pharmaceutical compositions and/or formulations of Trilaciclib and of Trilaciclib salts of the present disclosure, can be used as medicaments.

The present disclosure also provides methods of treating myelosuppression, particularly chemotherapy-induced myelosuppression, and more particularly for reducing chemotherapy-induced bone marrow suppression in patients with SCLC, NSCLC, colorectal cancer (particularly metastatic colorectal cancer), breast cancer (particularly metastatic triple-negative breast cancer), or bladder cancer (particularly advanced/metastatic bladder cancer); and particularly SCLC, by administering a therapeutically effective amount of any one or a combination of the crystalline polymorphs of Trilaciclib and/or Trilaciclib salts, and/or solvates of Trilaciclib or Trilaciclib salts, of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer: Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring with silicon low background.

All X-Ray Powder Diffraction peak values are calibrated with regard to standard silicon spiking in the sample.

EXAMPLES

Preparation of Starting Materials

Trilaciclib can be prepared according to methods known from the literature, for example U.S. Pat. No. 8,598,186.

Example 1: Preparation of Trilaciclib Form TT1

Trilaciclib (0.05 g) was dissolved in 7 mL Dichloromethane:Isopropanol (80:20, v/v) mixture at 50° C. The clear solution was cooled to 25° C. and 3 mL of n-heptane were added under magnetic stirring at 25° C. The reaction mixture was maintained for about 20 hours at 25° C. Solid obtained was filtered and dried under vacuum for 10-15 minutes. The obtained solid was analyzed by XRD and designated as Form TT1 of Trilaciclib (FIG. 1).

Example 2: Preparation of Trilaciclib Form TT2

Trilaciclib (0.5 g) was dissolved in 4 mL acetic acid at 25-30° C. To the clear solution, 3 mL n-heptane were added and the reaction mixture was maintained under stirring for about 20 hours at 25° C. Solid obtained was filtered and dried under vacuum for 10-15 minutes. The obtained solid was analyzed by XRD and designated as Trilaciclib Form TT2 (FIG. 2).

Example 3: Preparation of Trilaciclib Form TT3

Trilaciclib (0.5 g) was dissolved in 4 mL formic acid at 25-30° C. To the clear solution 3 mL n-heptane were added and the reaction mixture was maintained under stirring for about 20 hours at 25° C. Solid obtained was filtered and dried under vacuum for 10-15 minutes. The obtained solid was analyzed by XRD and designated as Trilaciclib Form TT3 (FIG. 3).

Example 4: Preparation of Trilaciclib Form TT4

Trilaciclib (0.5 g) was dissolved in 4 mL propionic acid at 25-30° C. To the clear solution 3 mL n-heptane were added and the reaction mixture was maintained under stirring for about 20 hours at 25° C. Solid obtained was filtered and dried under vacuum for 10-15 minutes. The obtained solid was analyzed by XRD and designated as Trilaciclib Form TT4 (FIG. 4).

Example 5: Preparation of Trilaciclib Trifluoroacetate Salt Form TTFA1

Trilaciclib (0.5 g) was dissolved in 4 mL trifluoroacetic acid at 25-30° C. To the clear solution 3 mL acetone were added and the reaction mixture was maintained under stirring for about 20 hours at 25° C. Solid obtained was filtered and dried under vacuum for 10-15 minutes. The obtained solid was analyzed by XRD and designated as Trilaciclib trifluoroacetate salt Form TTFA1 (FIG. 5).

Example 6: Preparation of Trilaciclib Dihydrochloride Salt Form THCl1

Trilaciclib (1.0 g) was dissolved in 200 mL Dichloromethane:Methanol (85:15; v/v) mixture at 60° C. The solution was cooled to 25° C. and 0.75 mL (2 mole equivalents) of IPA-HCl solution (about 18% Hydrochloric acid in Isopropanol) was added. The reaction mixture was stirred at 25° C. for about 20 hours. The reaction mass was filtered and dried under vacuum for 10-15 minutes. The obtained solid was analyzed by XRD and designated as Trilaciclib dihydrochloride salt Form THCl1 (FIG. 6).

Example 7: Preparation of Trilaciclib Hydrochloride Acid Salt Form THCl

Trilaciclib (2.0 g) was dissolved in 400 mL Dichloromethane:Methanol (80:20; v/v) mixture at 60° C. The solution was cooled to 25° C. and 0.8 mL (1 mole equivalent) of IPA-HCl solution (about 18% Hydrochloric acid in Isopropanol) was added. The reaction mixture was stirred at 25° C. for about 20 hours. To the reaction mixture 50 mL of acetone were added and stirred at 25° C. for about 1 hour. The reaction mass was filtered and dried under vacuum for 15-30 minutes at 25° C. The obtained solid was analyzed by XRD and designated as Trilaciclib hydrochloride salt Form THCl (FIG. 7).

Example 8: Preparation of Trilaciclib Citrate Salt Form TCT1

Trilaciclib (0.25 g) was dissolved in 50 mL Dichloromethane:Methanol (80:20; v/v) mixture at 60° C. Cooled the solution to 25° C. and added 107 mg of citric acid anhydrous (1 mole equivalent). The reaction mixture was stirred at 25° C. for about 20 hours. The reaction mixture was cooled to 5° C., 50 mL of acetone were added and the mixture was stirred for about 1 hour at 5° C. The reaction mass was filtered (at 5° C.) and dried under vacuum for 15-30 minutes at 25° C. The obtained solid analyzed by XRD and designated as Trilaciclib citrate salt Form TCT1 (FIG. 8).

Example 9: Preparation of Trilaciclib Sulphate Salt Form TS1

Trilaciclib (1.0 g) was dissolved in 200 mL Dichloromethane:Methanol (80:20; v/v) mixture at 60° C. The solution was cooled to 25° C. and 0.25 mL of sulphuric acid solution (98% solution, 2 mole equivalent) was added. The reaction mixture was stirred at 25° C. for about 20 hours. To the reaction mixture 50 mL of acetone were added and the mixture was stirred at 25° C. for about 1 hour. The reaction mass was filtered and dried under vacuum for 15-30 minutes at 25° C. The obtained solid was analyzed by XRD and designated as Trilaciclib sulphate salt Form TS1 (FIG. 9).

Example 10: Preparation of Trilaciclib Mesylate Salt Form TMSA1

Trilaciclib (0.25 g) was dissolved in 50 mL Dichloromethane:Methanol (80:20; v/v) mixture at 60° C. The solution was cooled to 25° C. and 0.08 mL of methane sulphonic acid (2 mole equivalent) was added. The reaction mixture was stirred at 25° C. for about 20 hours. The reaction mixture was cooled to 5° C., 50 mL of acetone were added and the mixture was stirred for about 1 hour at 5° C. The reaction mass was filtered (5° C.) and dried under vacuum for 15-30 minutes at 25° C. The obtained solid was analyzed by XRD and designated as Trilaciclib mesylate salt Form TMSA1 (FIG. 10).

Example 11: Preparation of Trilaciclib Besylate Salt Form TBSA1

Trilaciclib (0.25 g) was dissolved in 50 mL Dichloromethane:Methanol (80:20; v/v) mixture at 60° C. The solution was cooled to 25° C. and 88 mg of benzene sulphonic acid (1 mole equivalent) was added. The reaction mixture was stirred at 25° C. for about 20 hours. The reaction mixture was cooled to 5° C., 50 mL of acetone were added and the reaction was stirred for about 1 hour at 5° C. The reaction mass was filtered (at 5° C.) and dried under vacuum for 15-30 minutes at 25° C. The obtained solid was analyzed by XRD and designated as Trilaciclib besylate salt Form TBSA1 (FIG. 11).

Example 12: Preparation of Trilaciclib Dihydrochloride Salt Form THCl2

Trilaciclib (5 g) was stirred in a mixture of Dichloromethane:Methanol (80:20 v/v, 500 mL) at 25° C. for 15 minutes. A solution of hydrochloric acid in Isopropanol (about 18%, 4 mL) was added into the slurry mass to obtain a clear solution. The reaction mixture was stirred at 25° C. for about 3 hours. n-Heptane (1000 mL) was added dropwise over a period of time of 30 minutes. The obtained slurry was stirred at 25° C. for about 17 hours, filtered under vacuum over 90 minutes and dried at 45° C. in vacuum tray oven for 2 hours. The obtained solid analyzed by XRD and designated as Trilaciclib dihydrochloride salt Form THCl2.

Example 13: Preparation of Trilaciclib Dihydrochloride Salt Form THCl2

Trilaciclib (0.045 g) was suspended in 10 mL Dichloromethane:Ethanol (70:30; v/v) mixture and stirred for 30 minutes at 25° C. A solution of hydrochloric acid in Isopropanol (about 18%, 0.05 mL) was added into the slurry mass to obtain a clear solution. The reaction mixture was stirred about 4 hours at 25° C. The obtained solid was filtered, dried under vacuum for 10-15 minutes at 25° C. and analyzed by XRD-Trilaciclib dihydrochloride salt Form THCl2.

Example 14: Preparation of Trilaciclib Dihydrochloride Salt Form THCl2

Trilaciclib (0.2 g) was suspended in 20 mL of Dichloromethane:Methanol (80:20; v/v) mixture and stirred at 25° C. for 15 minutes. A solution of hydrochloric acid in Isopropanol (about 18%, 0.16 mL) was added into the slurry mass to obtain a clear solution. The reaction mixture was stirred at 25° C. for about 30 minutes. n-Heptane (100 mL) was added over 5 minutes. The obtained slurry mass was cooled to 5° C. and stirred at 5° C. for about 1 hour. The obtained slurry mass was filtered under vacuum at 5° C. and dried at 25° C. The obtained solid was analyzed by XRD and designated as Trilaciclib dihydrochloride salt Form THCl2 (FIG. 12).

Example 15: Preparation of Trilaciclib Dihydrochloride Salt Form THCl3

Trilaciclib (0.045 g) was suspended in 10 mL Dichloromethane:Dioxane (70:30; v/v) mixture and stirred for 30 minutes at 25° C. A solution of hydrochloric acid in Isopropanol (about 18%, 0.05 mL) was added and the reaction mixture was stirred for 20 hours at 25° C., filtered and dried under vacuum for 10-15 minutes. The obtained solid analyzed by XRD and designated as Trilaciclib dihydrochloride salt Form THCl3 (FIG. 13).

Example 16: Preparation of Trilaciclib Dihydrochloride Salt Form THCl1

Trilaciclib (0.045 g) was suspended in 10 mL Dichloromethane:Isopropanol (70:30, v/v) mixture at 25° C. A solution of hydrochloric acid in Isopropanol (about 18%, 0.05 mL) was added and the reaction mixture was stirred for 4 hours at 25° C., filtered and dried under vacuum for 10-15 minutes. The obtained solid analyzed by XRD-Trilaciclib dihydrochloride salt Form THCl1.

Example 17: Preparation of Trilaciclib Dihydrochloride Salt Form THCl4

Trilaciclib (0.045 g) was suspended in 10 mL Dichloromethane and stirred for 30 minutes at 25° C. A solution of hydrochloric acid in Isopropanol (about 18%, 0.05 mL) was added and the reaction mixture was stirred at 25° C. for about 20 hours. The reaction mass was filtered and dried under vacuum for 10-15 minutes at 25° C. The obtained solid was analyzed by XRD and designated as Trilaciclib dihydrochloride salt Form THCl4 (FIG. 14).

Example 18: Preparation of Trilaciclib Dihydrochloride Salt Form THCl4

Trilaciclib (0.045 g) was suspended in 10 mL Dichloromethane:Acetone (70:30; v/v) mixture and stirred for 30 minutes at 25° C. A solution of hydrochloric acid in Isopropanol (about 18%, 0.05 mL) was added and the reaction mixture was stirred at 25° C. for about 20 hours. The reaction mass was filtered and dried under vacuum for 10-15 minutes at 25° C. The obtained solid analyzed by XRD and designated as Trilaciclib dihydrochloride salt Form THCl4.

Example 19: Preparation of Trilaciclib Dihydrochloride Salt Form THCl5

Trilaciclib (0.045 g) was suspended in 10 mL Acetonitrile and stirred for 30 minutes at 25° C. A solution of hydrochloric acid in Isopropanol (about 18%, 0.05 mL) was added and the reaction mixture was stirred at 25° C. for about 20 hours. The reaction mass was filtered and dried under vacuum for 10-15 minutes at 25° C. The obtained solid was analyzed by XRD and designated as Trilaciclib Form THCl5.

Trilaciclib dihydrochloride salt Form THCl5 (FIG. 15).

Example 20: Preparation of Trilaciclib Dihydrochloride Salt Form THCl5

Trilaciclib (0.045 g) was suspended in 10 mL Dichloromethane:Acetonitrile (70:30; v/v) mixture and stirred for 30 minutes at 25° C. A solution of hydrochloric acid in Isopropanol (about 18%, 0.05 mL) was added and the reaction mixture was stirred at 25° C. for about 20 hours. The reaction mass was filtered and dried under vacuum for 10-15 minutes at 25° C. The obtained solid was analyzed by XRD and designated as Trilaciclib dihydrochloride salt Form THCl5.

Example 21: Preparation of Trilaciclib Dihydrochloride Salt Form THCl6

Trilaciclib (0.045 g) was suspended in 5 mL Acetonitrile at 0° C. A solution of hydrochloric acid in Isopropanol (about 18%, 0.05 mL) was added and the reaction mixture was stirred at 0° C. for about 20 hours. The reaction mass was filtered and dried under vacuum for 10-15 minutes at 25° C. The obtained solid was analyzed by XRD and designated as Trilaciclib dihydrochloride salt Form THCl6 (FIG. 16).

Example 22: Preparation of Trilaciclib Hydrobromide Salt Form THBr1

Trilaciclib (0.25 g) was suspended in 50 mL Methanol at 25° C. A solution of hydrobromic acid in water (48%, 0.25 mL) was added and the obtained clear solution was stirred at 25° C. for about 30 minutes; suspension was formed. Methyl tert-butyl ether (50 mL) was added and the reaction mixture was stirred at 25° C. for about 60 minutes. The reaction mass was filtered and dried under vacuum for 10-15 minutes at 25° C. The obtained solid was analyzed by XRD and designated as Trilaciclib hydrobromide salt Form THBr1 (FIG. 17).

Example 23: Preparation of Trilaciclib Dihydrochloride Salt Form THCl6

Trilaciclib dihydrochloride (THCl1*, 2.0 g) was dissolved in a mixture of methanol:water (70:30 (v/v); 100 mL) at 60° C. The solution was filtered to remove any undissolved particles and the clear solution was dropwise added into precooled methyl tert-butyl ether (300 ml) at about 0-5° C. under stirring. The reaction mixture was maintained under stirring at 0-5° C. for about 2-4 hour, filtered and dried under vacuum at 25° C. for about 30-60 minutes. The obtained solid was further dried under vacuum at 60° C. for 24 hours. After cooling to room temperature, the obtained solid was analyzed by XRD-Trilaciclib dihydrochloride salt Form THCl6.

Further aspects and embodiments of the present disclosure are set out in the following numbered clauses:

1. A crystalline form of Trilaciclib, designated TT1, which is characterized by data selected from one or more of the following: an X-ray powder diffraction pattern substantially as depicted in FIG. 1; an X-ray powder diffraction pattern having peaks at 5.6, 10.7, 11.5, 17.4 and 23.1 degrees 2-theta±0.2 degrees 2-theta; and combinations of these data.
2. Crystalline Form TT1 of Trilaciclib according to clause 1 which is further characterized by an X-ray powder diffraction pattern having peaks at 5.6, 10.7, 11.5, 17.4 and 23.1 degrees 2-theta±0.2 degrees 2-theta, and also having any one, two, three or four additional peaks selected from 18.5, 19.0, 21.5 and 24.4 degrees 2-theta±0.2 degrees 2-theta.
3. Crystalline Form TT1 of Trilaciclib according to clause 1 or clause 2, which is characterized by an X-ray powder diffraction pattern having peaks at 5.6, 10.7, 11.5, 17.4, 18.5, 19.0, 21.5, 23.1, and 24.4 degrees 2-theta±0.2 degrees 2-theta.
4. Crystalline Form TT1 of Trilaciclib according to any of clauses 1, 2 or 3, which is isolated.
5. A crystalline form of Trilaciclib, designated Form TT2, which is characterized by data selected from one or more of the following: an X-ray powder diffraction pattern substantially as depicted in FIG. 2; an X-ray powder diffraction pattern having peaks at 8.1, 9.1, 11.0, 14.5 and 15.9 degrees 2-theta±0.2 degrees 2-theta; and combinations of these data.
6. Crystalline Form TT2 of Trilaciclib according to clause 5, which is characterized by an X-ray powder diffraction pattern having peaks at 8.1, 9.1, 11.0, 14.5 and 15.9 degrees 2-theta±0.2 degrees 2-theta, and also having any one, two, three or four additional peaks selected from 19.6, 20.2, 22.1 and 27.2 degrees 2-theta±0.2 degrees 2-theta.
7. Crystalline Form TT2 of Trilaciclib according to clause 5 or clause 6, which is characterized by an X-ray powder diffraction pattern having peaks at 8.1, 9.1, 11.0, 14.5, 15.9, 19.6, 20.2, 22.1, and 27.degrees 2-theta±0.2 degrees 2-theta.
8. Crystalline Form TT2 of Trilaciclib according to any of clauses 5, 6 or 7, which is isolated.
9. Crystalline Form TT2 of Trilaciclib according to any of clauses 5, 6, 7, or 8, which is an acetic acid solvate.
10. Crystalline Form TT2 according to any of clauses 5, 6, 7, or 8, which is a salt of Trilaciclib with acetic acid (i.e., Trilaciclib acetate salt).
11. Crystalline Form TT2 of Trilaciclib according to any of clauses 5, 6, 7, 8, 9, or 10, wherein the mole ratio of Trilaciclib to acetic acid is 1:2
12. An acetic acid solvate of Trilaciclib.
13. An acetic acid solvate of Trilaciclib according to clause 12, wherein the mole ratio of Trilaciclib to acetic acid is 1:2.
14. Trilaciclib acetic acid salt.

15. Trilaciclib acetic salt according to clause 14, wherein the mole ratio of Trilaciclib to acetic acid is 1:2.
16. Acetic acid solvate of Trilaciclib according to clause 12 or clause 13, or Trilaciclib acetic acid salt according to clause 14 or clause 15, which is crystalline.
17. A crystalline form of Trilaciclib, designated Form TT3, which is characterized by data selected from one or more of the following: an X-ray powder diffraction pattern substantially as depicted in FIG. 3; an X-ray powder diffraction pattern having peaks at 5.3, 10.2, 10.8, 17.8 and 25.2 degrees 2-theta±0.2 degrees 2-theta; and combinations of these data.
18. Crystalline Form TT3 of Trilaciclib according to clause 17, which is further characterized by an X-ray powder diffraction pattern having peaks at 5.3, 10.2, 10.8, 17.8 and 25.2 degrees 2-theta±0.2 degrees 2-theta, and also having any one, two, three or four additional peaks selected from 15.3, 18.6, 23.6 and 24.0 degrees 2-theta±0.2 degrees 2-theta.
19. Crystalline Form TT3 of Trilaciclib according to clause 17 or clause 18, which is characterized by an X-ray powder diffraction pattern having peaks at 5.3, 10.2, 10.8, 15.3, 17.8, 18.6, 23.6, 24.0, and 25.2 degrees 2-theta±0.2 degrees 2-theta.
20. Crystalline Form TT3 of Trilaciclib according to any of clauses 17, 18 or 19, which is isolated.
21. Crystalline Form TT3 of Trilaciclib according to any of clauses 17, 18, 19, or 20, which is a formic acid solvate.
22. Crystalline Form TT3 of Trilaciclib according to any of clauses 17, 18, 19, or 20, which is a salt of Trilaciclib with formic acid (i.e., Trilaciclib formic salt).
23. Crystalline Form TT3 of Trilaciclib according to any of clauses 17, 18, 19, 20, 21, or 22, wherein the mole ratio of Trilaciclib to formic acid is 1:2.
24. A formic acid solvate of Trilaciclib.
25. A formic acid solvate of Trilaciclib according to clause 24, wherein the mole ratio of Trilaciclib to formic acid is 1:2
26. Trilaciclib formic acid salt.
27. Trilaciclib formic acid salt according to clause 26, wherein the mole ratio of Trilaciclib to formic acid is 1:2
28. Formic acid solvate of Trilaciclib according to clause 24 or 25, or Trilaciclib formic acid salt according to clause 26 or 27, which is crystalline.
29. A crystalline form of Trilaciclib, designated Form TT4 which is characterized by data selected from one or more of the following: an X-ray powder diffraction pattern substantially as depicted in FIG. 4; an X-ray powder diffraction pattern having peaks at 13.1, 18.1, 19.1, 20.9 and 23.3 degrees 2-theta±0.2 degrees 2-theta; and combinations of these data.
30. Crystalline Form TT4 of Trilaciclib according to clause 29, which is further characterized by an X-ray powder diffraction pattern having peaks at 13.1, 18.1, 19.1, 20.9 and 23.3 degrees 2-theta±0.2 degrees 2-theta, and also having any one, two, three or four additional peaks selected from 7.1, 9.7, 22.4 and 27.4 degrees 2-theta±0.2 degrees 2-theta.
31. Crystalline Form TT4 of Trilaciclib according to clause 29 or clause 30, which is characterized by an X-ray powder diffraction pattern having peaks at 7.1, 9.7, 13.1, 18.1, 19.1, 20.9, 22.4, 23.3, and 27.4 degrees 2-theta±0.2 degrees 2-theta.
32. Crystalline Form TT4 of Trilaciclib according to any of clauses 29, 30 or 31, which is isolated.
33. Crystalline Form TT4 of Trilaciclib according to any of clauses 29, 30, 31, or 32, which is a propionic acid solvate.
34. Crystalline Form TT4 of Trilaciclib according to any of clauses 29, 30, 31, or 32, which is a salt with propionic acid (i.e., Trilaciclib propionate salt).
35. Crystalline Form TT4 of Trilaciclib according to clause 33 or clause 34, wherein the mole ratio of Trilaciclib to propionic acid is 1:2.
36. A propionic acid solvate of Trilaciclib.
37. A propionic acid solvate of Trilaciclib according to clause 36, wherein the mole ratio of Trilaciclib to propionic acid is 1:2.
38. Trilaciclib propionic acid salt.
39. Trilaciclib propionic acid salt according to clause 38, wherein the mole ratio of Trilaciclib to propionic acid is 1:2.
40. Propionic acid solvate of Trilaciclib according to clause 36 or 37, or Trilaciclib propionic acid salt according to clause 38 or 39, which is crystalline.
41. A crystalline form of Trilaciclib trifluoroacetate salt, designated Form TTFA1, which is characterized by data selected from one or more of the following: an X-ray powder diffraction pattern substantially as depicted in FIG. 5; an X-ray powder diffraction pattern having peaks at 5.8, 16.2, 17.7, 18.4 and 26.7 degrees 2-theta±0.2 degrees 2-theta; and combinations of these data.
42. Crystalline Form TTFA1 of Trilaciclib trifluoroacetic acid salt according to clause 41, which is further characterized by an X-ray powder diffraction pattern having peaks at 5.8, 16.2, 17.7, 18.4 and 26.7 degrees 2-theta±0.2 degrees 2-theta, and also having any one, two, three or four additional peaks selected from 8.9, 14.1, 26.0 and 36.0 degrees 2-theta±0.2 degrees 2-theta.
43. Crystalline Form TTFA1 of Trilaciclib trifluoroacetic acid salt according to clause 41 or clause 42, which is characterized by an X-ray powder diffraction pattern having peaks at 5.8, 8.9, 14.1, 16.2, 17.7, 18.4, 26.0, 26.7, and 36.0 degrees 2-theta±0.2 degrees 2-theta.
44. Crystalline Form TTFA1 of Trilaciclib trifluoroacetic acid salt according to any of clauses 41, 42 or 43, which is isolated.
45. Crystalline Form TTFA1 of Trilaciclib trifluoroacetic acid salt according to any of clauses 41, 42, 43, or 44, wherein the mole ratio of Trilaciclib to trifluoroacetic acid is 1:2.
46. A salt of Trilaciclib with trifluoroacetic acid.
47. A salt of Trilaciclib with trifluoroacetic acid according to clause 46, wherein the mole ratio of Trilaciclib to trifluoroacetic acid is 1:2.
48. A crystalline form of Trilaciclib dihydrochloride salt designated Form THCl1 is characterized by data selected from one or more of the following: an X-ray powder diffraction pattern substantially as depicted in FIG. 6; an X-ray powder diffraction pattern having peaks at 8.3, 9.4, 12.0, 19.1 and 21.1 degrees 2-theta±0.2 degrees 2-theta; and combinations of these data.
49. Crystalline Form THCl1 of Trilaciclib dihydrochloride salt according to clause 48, which is further characterized by an X-ray powder diffraction pattern having peaks at 8.3, 9.4, 12.0, 19.1 and 21.1 degrees 2-theta±0.2 degrees 2-theta, and also having any one, two, three or four additional peaks selected from 4.1, 10.0, 12.6 and 23.8 degrees 2-theta±0.2 degrees 2-theta.

50. Crystalline Form THCl1 of Trilaciclib dihydrochloride salt according to clause 48 or clause 49, which is characterized by an X-ray powder diffraction pattern having peaks at 4.1, 8.3, 9.4, 10.0, 12.0, 12.6, 19.1, 21.1, and 23.8 degrees 2-theta±0.2 degrees 2-theta.

51. Crystalline Form THCl1 of Trilaciclib dihydrochloride salt according to any of clauses 48, 49, or 50, which is isolated.

52. A product according to any of clauses 48, 49, 50, or 51, which is a hydrate, optionally a hemihydrate, a monohydrate, a dihydrate, a trihydrate, a tetrahydrate, a pentahydrate, or a hexahydrate.

53. A crystalline form of Trilaciclib hydrochloride salt, designated Form THCl, which is characterized by data selected from one or more of the following: an X-ray powder diffraction pattern substantially as depicted in FIG. 7; an X-ray powder diffraction pattern having peaks at 6.2, 8.5, 13.6, 14.1 and 21.7 degrees 2-theta±0.2 degrees 2-theta; and combinations of these data.

54. Crystalline Form THCl of Trilaciclib hydrochloride salt according to clause 53, which is characterized by an X-ray powder diffraction pattern having peaks at 6.2, 8.5, 13.6, 14.1 and 21.7 degrees 2-theta±0.2 degrees 2-theta, and also having any one, two, three or four additional peaks selected from 12.3, 17.9, 18.7 and 19.4 degrees 2-theta±0.2 degrees 2-theta.

55. Crystalline Form THCl of Trilaciclib hydrochloride salt according to clause 53 or clause 54, which is characterized by an X-ray powder diffraction pattern having peaks at 6.2, 8.5, 12.3, 13.6, 14.1, 17.9, 18.7, 19.4, and 21.7 degrees 2-theta±0.2 degrees 2-theta.

56. Crystalline Form THCl of Trilaciclib hydrochloride salt according to any of clauses 53, 54 or 55, wherein the ratio of Trilaciclib to hydrochloric acid is 1:1.

57. Crystalline Form THCl of Trilaciclib hydrochloride salt according to any of clauses 53, 54, 55, or 56, which is isolated.

58. A crystalline form of Trilaciclib citrate salt, designated Form TCT1, which is characterized by data selected from one or more of the following: an X-ray powder diffraction pattern substantially as depicted in FIG. 8; an X-ray powder diffraction pattern having peaks at 6.1, 7.3, 11.3, 15.3 and 19.3 degrees 2-theta±0.2 degrees 2-theta; and combinations of these data.

59. Crystalline Form TCT1 of Trilaciclib citrate salt according to clause 58, which is further characterized by an X-ray powder diffraction pattern having peaks at 6.1, 7.3, 11.3, 15.3 and 19.3 degrees 2-theta±0.2 degrees 2-theta, and also having any one, two, three or four additional peaks selected from 8.9, 9.3, 20.4 and 22.7 degrees 2-theta±0.2 degrees 2-theta.

60. Crystalline Form TCT1 of Trilaciclib citrate salt according to clause 58 or clause 59, which is characterized by an X-ray powder diffraction pattern having peaks at 6.1, 7.3, 8.9, 9.3, 11.3, 15.3, 19.3, 20.4, and 22.7 degrees 2-theta±0.2 degrees 2-theta.

61. Crystalline Form TCT1 of Trilaciclib citrate salt according to any of clauses 58, 59 or 60, wherein the mole ratio of Trilaciclib to citric acid is from 1:0.5 to 1:2; preferably the ratio is 1:1.

62. Crystalline Form TCT1 of Trilaciclib citrate salt according to any of clauses 58, 59, 60, or 61, which is isolated.

63. Trilaciclib citric acid salt.

64. Trilaciclib citric acid salt according to clause 63, which is crystalline.

65. Trilaciclib citric acid salt according to clause 63 or clause 64, wherein the molar ratio of Trilaciclib to citric acid is from 1:0.5 to 1:2; preferably 1:1.

66. A product according to any of clauses 53, 54, 55, 56, or 57, which is a hydrate, optionally a hemihydrate, a monohydrate, a dihydrate, a trihydrate, a tetrahydrate, a pentahydrate, or a hexahydrate.

67. A process for preparing Trilaciclib citrate salt as defined in any of clauses 58, 59, 60, 61, 62, 63, 64, or 65, comprising combining a mixture of Trilaciclib citrate in a solvent with an antisolvent 68. A process according to clause 67, wherein the mixture of Trilaciclib citrate in a solvent is prepared by combining a solution of Trilaciclib in a solvent, with citric acid (preferably 1 mole equivalent of citric acid, preferably wherein the citric acid is anhydrous).

69. A process according to clause 67 or clause 68, wherein the solvent is a chlorinated hydrocarbon (preferably a chlorinated $C_{1-4}$ hydrocarbon, more preferably dichloromethane), or an alcohol (preferably a $C_{1-6}$ alcohol, more preferably methanol), or a mixture thereof.

70. A process according to any of clauses 67, 68 or 69, wherein the solvent is a mixture of a chlorinated hydrocarbon (preferably a chlorinated $C_{1-4}$ hydrocarbon, more preferably dichloromethane), or an alcohol (preferably a $C_{1-6}$ alcohol, more preferably methanol), particularly wherein the solvent is a mixture of dichloromethane and methanol.

71. A process according to clause 70, wherein the vol/vol ratio of chlorinated hydrocarbon (preferably a chlorinated $C_{1-4}$ hydrocarbon, more preferably dichloromethane), or an alcohol (preferably a $C_{1-6}$ alcohol, more preferably methanol) is: about 10:1 to about 1:10, about 8:1 to about 1:1, about 6:1 to about 2:1, about 5:1 to about 3:1, or about 4:1.

72. A process according to clause 71, wherein the solvent is a mixture of dichloromethane and methanol in a vol/vol ratio of: about 8:1 to about 1:1, about 6:1 to about 2:1, about 5:1 to about 3:1, or about 4:1.

73. A process according to any of clauses 67, 68, 69, 70, 71, or 72, wherein the antisolvent is a ketone, preferably a $C_{3-6}$ ketone, and more preferably acetone.

74. A process according to any of clauses 67, 68, 69, 70, 71, 72, or 73, wherein the vol/vol ratio of solvent to antisolvent is: about 4:1 to about 1:4, about 3:1 to about 1:3, about 2:1 to about 1:2, or about 1:1.

75. A process according to any of clauses, 67, 68, 69, 70, 71, 72, 73, or 74, wherein the antisolvent is added to the solution of Trilaciclib citrate in the solvent.

76. A process according to any of clauses 67, 68, 69, 70, 71, 72, 73, 74, or 75, wherein the mixture of Trilaciclib citrate in the solvent is combined with the antisolvent at a temperature of: about −5° C. to about 20° C., about −2° C. to about 15° C., about 0° C. to about 10° C., about 2° C. to about 8° C., or about 5° C.

77. A process according to any of clauses 67, 68, 69, 70, 71, 72, 73, 74, 75, or 76, wherein after combining the mixture of Trilaciclib citrate in the solvent with the antisolvent, the reaction mixture is stirred at a temperature of: about −5° C. to about 20° C., about −2° C. to about 15° C., about 0° C. to about 10° C., about 2° C. to about 8° C., or about 5° C.

78. A process according to any of clauses 67, 68, 69, 70, 71, 72, 73, 74, 75, 76, or 77, wherein after combining the mixture of Trilaciclib citrate in the solvent with the antisolvent, the reaction mixture is stirred for a period of: about 0.4 hours to about 6 hours, about 0.6 hours to about 3 hours, about 0.8 to about 1.5 hours, or about 1 hour.

79. A process according to any of clauses 67, 68, 69, 70, 71, 72, 73, 74, 75, 76, 77, or 78, wherein the product is isolated, optionally by centrifugation, decantation, or filtration, preferably by filtration.

80. A process according to clause 79, wherein the product is dried, optionally under reduced pressure, and optionally at a temperature of: about 18° C. to about 60° C., about 20° C. to about 40° C., about 22° C. to about 30° C., about 24 to about 28° C., or about 25° C.

81. A process according to clause 80, wherein the drying is for a period of time of: about 5 minutes to about 60 minutes, about 10 minutes to about 45 minutes, or about 15 minutes to about 30 minutes.

82. A product obtainable by the process of any of clauses 67, 68, 69, 70, 71, 72, 73, 74, 75, 76, 77, 78, 79, 80, or 81.

83. A crystalline form of Trilaciclib sulphate salt, designated Form TS1, which is characterized by data selected from one or more of the following: an X-ray powder diffraction pattern substantially as depicted in FIG. 9; an X-ray powder diffraction pattern having peaks at 10.9, 13.5, 17.0, 20.1 and 25.2 degrees 2-theta±0.2 degrees 2-theta; and combinations of these data.

84. Crystalline Form TS1 of Trilaciclib sulphate salt according to clause 83, which is further characterized by an X-ray powder diffraction pattern having peaks at 10.9, 13.5, 17.0, 20.1 and 25.2 degrees 2-theta±0.2 degrees 2-theta, and also having any one, two, three or four additional peaks selected from 6.6, 8.2, 18.2 and 18.6 degrees 2-theta±0.2 degrees 2-theta.

85. Crystalline Form TS1 of Trilaciclib sulphate salt according to clause 83 or clause 84, which is characterized by an X-ray powder diffraction pattern having peaks at 6.6, 8.2, 10.9, 13.5, 17.0, 18.2, 18.6, 20.1, and 25.2 degrees 2-theta±0.2 degrees 2-theta.

86. Crystalline Form TS1 of Trilaciclib sulphate salt according to any of clauses 83, 84 or 85, wherein the mole ratio of Trilaciclib to sulfuric acid is 1:1.

87. Crystalline Form TS1 of Trilaciclib sulphate salt according to any of clauses 83, 84, 85, or 86, which is isolated.

88. Trilaciclib sulphate salt.

89. Trilaciclib sulphate salt according to clause 88, which is crystalline.

90. Trilaciclib sulphate salt according to clause 88 or clause 89, wherein the mole ratio of Trilaciclib to sulfuric acid is 1:1.

91. A crystalline form of Trilaciclib mesylate salt, designated Form TMSA1, which is characterized by data selected from one or more of the following: an X-ray powder diffraction pattern substantially as depicted in FIG. 10; an X-ray powder diffraction pattern having peaks at 13.6, 15.8, 23.1, 25.1 and 28.2 degrees 2-theta±0.2 degrees 2-theta; and combinations of these data.

92. Crystalline Form TMSA1 of Trilaciclib mesylate salt according to clause 91, which is characterized by an X-ray powder diffraction pattern having peaks at 13.6, 15.8, 23.1, 25.1 and 28.2 degrees 2-theta±0.2 degrees 2-theta, and also having any one, two, three or four additional peaks selected from 6.0, 17.6, 18.2 and 22.4 degrees 2-theta±0.2 degrees 2-theta.

93. Crystalline Form TMSA1 of Trilaciclib mesylate salt according to clause 91 or clause 92, which is characterized by an X-ray powder diffraction pattern having peaks at 6.0, 13.6, 15.8, 17.6, 18.2, 22.4, 23.1, 25.1, and 28.2 degrees 2-theta±0.2 degrees 2-theta.

94. Crystalline Form TMSA1 of Trilaciclib mesylate salt according to any of clauses 91, 93 or 93, wherein the mole ratio of Trilaciclib to methanesulfonic acid is 1:1.

95. Crystalline Form TMSA1 of Trilaciclib mesylate salt according to any of clauses 91, 92, 93, or 94, which is isolated.

96. Trilaciclib methanesulfonic acid salt.

97. Trilaciclib methanesulfonic acid salt according to clause 96, which is crystalline.

98. Trilaciclib methanesulfonic acid salt according to clause 6 or clause 97, wherein the mole ratio of Trilaciclib to methanesulfonic acid is 1:1.

99. A crystalline form of Trilaciclib besylate salt, designated Form TBSA1, which is characterized by data selected from one or more of the following: an X-ray powder diffraction pattern substantially as depicted in FIG. 11; an X-ray powder diffraction pattern having peaks at 9.1, 11.5, 13.4, 19.4 and 22.8 degrees 2-theta±0.2 degrees 2-theta; and combinations of these data.

100. Crystalline Form TBSA1 of Trilaciclib besylate salt according to clause 99, which is characterized by an X-ray powder diffraction pattern having peaks at 9.1, 11.5, 13.4, 19.4 and 22.8 degrees 2-theta±0.2 degrees 2-theta, and also having any one, two, three or four additional peaks selected from 18.1, 18.4, 20.4 and 23.9 degrees 2-theta±0.2 degrees 2-theta.

101. Crystalline Form TBSA1 of Trilaciclib besylate salt according to clause 99 or clause 100, which is characterized by an X-ray powder diffraction pattern having peaks at 9.1, 11.5, 13.4, 18.1, 18.4, 19.4, 20.4, 22.8, and 23.9 degrees 2-theta±0.2 degrees 2-theta.

102. Crystalline Form TBSA1 of Trilaciclib besylate salt according to any of clauses 99, 100 or 101, wherein the mole ratio of Trilaciclib to benzenesulfonic acid is 1:1.

103. Crystalline Form TBSA1 of Trilaciclib besylate salt according to any of clauses 99. 100, 101, or 102, which is isolated.

104. Trilaciclib benzenesulfonic acid salt.

105. Trilaciclib benzenesulfonic acid salt according to clause 104, which is crystalline.

106. Trilaciclib benzenesulfonic acid salt according to clause 104 or clause 105, wherein the mole ratio of Trilaciclib to benzenesulfonic acid is 1:1.

107. A crystalline form of Trilaciclib dihydrochloride salt, designated Form THCl2, which is characterized by data selected from one or more of the following: an X-ray powder diffraction pattern substantially as depicted in FIG. 12; an X-ray powder diffraction pattern having peaks at 12.9, 16.3, 19.6, 27.6 and 33.2 degrees 2-theta±0.2 degrees 2-theta; and combinations of these data.

108. Crystalline Form THCl2 of Trilaciclib dihydrochloride salt according to clause 107, which is further characterized by an X-ray powder diffraction pattern having peaks at 12.9, 16.3, 19.6, 27.6 and 33.2 degrees 2-theta±0.2 degrees 2-theta, and also having any one, two, three or four additional peaks selected from 8.0, 14.6, 17.0 and 18.0 degrees 2-theta±0.2 degrees 2-theta.

109. Crystalline Form THCl2 of Trilaciclib dihydrochloride salt according to clause 107 or clause 108 which is characterized by an X-ray powder diffraction pattern having peaks at 8.0, 12.9, 14.6, 16.3, 17.0, 18.0, 19.6, 27.6, and 33.2 degrees 2-theta±0.2 degrees 2-theta.

110. Crystalline Form THCl2 of Trilaciclib dihydrochloride salt according to any of clauses 107, 108 or 109, which is isolated.

111. A crystalline form of Trilaciclib dihydrochloride salt, designated Form THCl3, which is characterized by data selected from one or more of the following: an X-ray powder diffraction pattern substantially as depicted in FIG. 13; an X-ray powder diffraction pattern having peaks at 6.6, 11.0, 16.1, 26.3 and 27.2 degrees 2-theta±0.2 degrees 2-theta; and combinations of these data.

112. Crystalline Form THCl3 of Trilaciclib dihydrochloride salt according to clause 111, which is further characterized by an X-ray powder diffraction pattern having peaks at 6.6, 11.0, 16.1, 26.3 and 27.2 degrees 2-theta±0.2 degrees 2-theta, and also having any one, two, three or four additional peaks selected from 18.1, 20.5, 23.0 and 28.3 degrees 2-theta±0.2 degrees 2-theta.

113. Crystalline Form THCl3 of Trilaciclib dihydrochloride salt according to clause 111 or clause 112, which is characterized by an X-ray powder diffraction pattern having peaks at 6.6, 11.0, 16.1, 18.1, 20.5, 23.0, 26.3, 27.2, and 28.3 degrees 2-theta±0.2 degrees 2-theta.

114. Crystalline Form THCl3 of Trilaciclib dihydrochloride salt according to any of clauses 111, 112 or 113, which is isolated.

115. Crystalline form of Trilaciclib dihydrochloride according to any of clauses 109, 110, 111, 112, 113, or 114, which is a hydrate, optionally a hemihydrate, a monohydrate, a dihydrate, a trihydrate, a tetrahydrate, a pentahydrate, or a hexahydrate.

116. A crystalline form of Trilaciclib dihydrochloride salt, designated Form THCl4, which is characterized by data selected from one or more of the following: an X-ray powder diffraction pattern substantially as depicted in FIG. 14; an X-ray powder diffraction pattern having peaks at 6.3, 8.5, 13.5, 19.4 and 26.9 degrees 2-theta±0.2 degrees 2-theta; and combinations of these data.

117. Crystalline Form THCl4 of Trilaciclib dihydrochloride salt according to clause 116, which is further characterized by an X-ray powder diffraction pattern having peaks at 6.3, 8.5, 13.5, 19.4 and 26.9 degrees 2-theta±0.2 degrees 2-theta, and also having any one, two, three or four additional peaks selected from 14.7, 17.1, 27.6 and 28.2 degrees 2-theta±0.2 degrees 2-theta.

118. Crystalline Form THCl4 of Trilaciclib dihydrochloride salt according to clause 116 or clause 117, which is characterized by an X-ray powder diffraction pattern having peaks at 6.3, 8.5, 13.5, 14.7, 17.1, 19.4, 26.9, 27.6 and 28.2 degrees 2-theta±0.2 degrees 2-theta.

119. Crystalline Form THCl4 of Trilaciclib dihydrochloride salt according to any of clauses 116, 117 or 118, which is isolated.

120. A crystalline form of Trilaciclib dihydrochloride salt, designated Form THCl5, which is characterized by data selected from one or more of the following: an X-ray powder diffraction pattern substantially as depicted in FIG. 15; an X-ray powder diffraction pattern having peaks at 6.1, 9.6, 14.7, 18.4 and 27.9 degrees 2-theta±0.2 degrees 2-theta; and combinations of these data.

121. Crystalline Form THCl5 of Trilaciclib dihydrochloride salt according to clause 120, which is further characterized by an X-ray powder diffraction pattern having peaks at 6.1, 9.6, 14.7, 18.4 and 27.9 degrees 2-theta±0.2 degrees 2-theta, and also having any one, two or three additional peaks selected from 18.0, 20.3 and 29.5 degrees 2-theta±0.2 degrees 2-theta.

122. Crystalline Form THCl5 of Trilaciclib dihydrochloride salt according to clause 120 or clause 121, which is characterized by an X-ray powder diffraction pattern having peaks at 6.1, 9.6, 14.7, 18.0, 18.4, 20.3, 27.9, and 29.5 degrees 2-theta±0.2 degrees 2-theta.

123. Crystalline Form THCl5 of Trilaciclib dihydrochloride salt according to any of clauses 120, 121 or 122, which is isolated.

124. A crystalline form of Trilaciclib dihydrochloride salt, designated form THCl6, which is characterized by data selected from one or more of the following: an X-ray powder diffraction pattern substantially as depicted in FIG. 16; an X-ray powder diffraction pattern having peaks at 7.3, 18.9, 23.3, 27.7 and 29.2 degrees 2-theta±0.2 degrees 2-theta; and combinations of these data.

125. Crystalline Form THCl6 of Trilaciclib dihydrochloride salt according to clause 124, which is further characterized by an X-ray powder diffraction pattern having peaks at 7.3, 18.9, 23.3, 27.7 and 29.2 degrees 2-theta±0.2 degrees 2-theta, and also having any one, two, three or four additional peaks selected from 8.1, 13.5, 16.2 and 21.1 degrees 2-theta±0.2 degrees 2-theta.

126. Crystalline Form THCl6 of Trilaciclib dihydrochloride salt according to clause 124 or clause 125, which is characterized by an X-ray powder diffraction pattern having peaks at 7.3, 8.1, 13.5, 16.2, 18.9, 21.1, 23.3, 27.7 and 29.2 degrees 2-theta±0.2 degrees 2-theta.

127. Crystalline Form THCl6 of Trilaciclib dihydrochloride salt according to any of clauses 124, 125 or 126, which is further characterized by an absence of peaks at 2.5-6.2 degrees 2-theta±0.2 degrees 2-theta.

129. Crystalline Form THCl6 of Trilaciclib dihydrochloride salt according to any of clauses 124, 125, 126, or 127, which is further characterized by an absence of peaks at 10.5-10.8 degrees 2-theta±0.2 degrees 2-theta.

130. Crystalline Form THCl6 of Trilaciclib dihydrochloride salt according to any of clauses 124, 125, 126, 127, 127, or 129, which is further characterized by an absence of peaks at 12.5-12.8 degrees 2-theta±0.2 degrees 2-theta.

131. Crystalline Form THCl6 of Trilaciclib dihydrochloride salt according to any of clauses 124, 125, 126, 127, 129, or 130, which is isolated.

132. A crystalline Trilaciclib dihydrochloride salt.

133. Crystalline Trilaciclib dihydrochloride salt according to any of clauses 116, 117, 118, 119, or 132 which is a hydrate, optionally a hemihydrate, a monohydrate, a dihydrate, a trihydrate, a tetrahydrate, a pentahydrate, or a hexahydrate, particularly a trihydrate, a tetrahydrate, a pentahydrate, or a hexahydrate, and more particularly a tetrahydrate or a pentahydrate.

134. A process for preparing a product as defined in any of clauses 124, 125, 126, 127, 128, 129, 130, 131, 132, or 133, which comprises combining a solution of Trilaciclib dihydrochloride in a solvent with an anti-solvent.

135. A process according to clause 134, wherein the solvent is selected from alcohols, water, and mixtures thereof, optionally wherein the solvent is a mixture of an alcohol (preferably a $C_1$ to $C_4$ alcohol, and more particularly methanol) and water.

136. A process according to clause 135, wherein the solvent is a mixture of an alcohol (preferably a $C_1$ to $C_4$ alcohol, and more particularly methanol) and water and wherein the ratio of alcohol:water, preferably methanol:water is from: about 4:1 to about 1:4, about 3.5:1 to about 1:3.5, about 3:1 to about 3:1 to about 1:3; about 2.5:1 to about 1:1.5, about 2.4:1 to about 1:1, or about 2.4:1 to about 2.3:1.

137. A process according to any of clauses 133, 134, 135, or 136, wherein the antisolvent is an ether, an ester or an alkane.

138. A process according to any of clauses 133, 134, 135, 136, or 137, wherein the antisolvent is a $C_{4-8}$ ether (preferably methyl tert-butyl ether or diisopropyl ether), a $C_{5-8}$ straight or branched alkane (more preferably heptane or hexane), or a $C_{2-5}$ ester (preferably ethyl acetate).

139. A process according to clause 138, wherein the antisolvent is an ether, preferably a $C_{4-8}$ ether, and more particularly methyl tert-butyl ether.

140. A process according to any of clauses 133, 134, 135, 136, 137, 138, or 139, wherein the antisolvent is added to the solution, or the solution may be added to the antisolvent (reverse addition).

141. A process according to any of clauses 133, 134, 135, 136, 137, 138, 139, or 140, wherein the solution is added to the antisolvent.

142. A process according to any of clauses 133, 134, 135, 136, 137, 138, 139, 140, or 141, wherein the antisolvent is pre-cooled prior to combining with the solution.

143. A process according to any of clauses 133, 134, 135, 136, 137, 138, 139, 140, 141, or 142, wherein the solution is added slowly, preferably dropwise, to the antisolvent.

144. A process according to any of clauses 133, 134, 135, 136, 137, 138, 139, 140, 141, 142, or 143, wherein the solvent is added dropwise to a precooled antisolvent.

145. A process according to any of clauses 133, 134, 135, 136, 137, 138, 139, 140, 141, 142, 143, or 144, wherein the antisolvent is pre-cooled at a temperature of: about −5° C. to about 15° C., about −2° C. to about 10° C., or about 0° C. to about 5° C.

146. A process according to any of clauses 133, 134, 135, 136, 137, 138, 139, 140, 141, 142, 143, 144, or 145 139, wherein the mixture is stirred during the combining of the solution of Trilaciclib dihydrochloride in the solvent with the antisolvent.

147. A process according to any of clauses 133, 134, 135, 136, 137, 138, 139, 140, 141, 142, 143, 144, 145, or 146, wherein the antisolvent:solvent ratio (v/v) is about 15:1 to about 1:5, about 10:1 to about 1:5, about 8:1 to about 1:2, about 5:1 to about 1:1, about 4:1 to about 2:1, about 3.5:1 to about 3:1 or about 3:1.

148. A process according to any of clauses 133, 134, 135, 136, 137, 138, 139, 140, 141, 142, 143, 144, 145, 146, or 147, wherein following combining the solution of Trilaciclib dihydrochloride with the antisolvent, the mixture is stirred under cooling.

149. A process according to clause 148, wherein the cooling is to: about −5° C. to about 15° C., about −2° C. to about 10° C., or about 0° C. to about 5° C.

150. A process according to clause 148 or clause 149 wherein the stirring is carried out over a period of about 0.5 hours to about 10 hours, about 0.7 hours to about 8 hours, about 1 hour to about 6 hours, or about 2 hours to about 4 hours.

151. A process according to any of clauses 133, 134, 135, 136, 137, 138, 139, 140, 141, 142, 143, 144, 145, 146, 147, 148, 149, or 150, which further comprises isolating the Trilaciclib dihydrochloride Form THCl6, optionally by centrifugation, decantation, or filtration, preferably by filtration.

152. A process according to clause 151, wherein the product is dried, preferably under reduced pressure.

153. A process according to clause 152, wherein the drying is carried out at elevated temperature, preferably at a temperature of: about 30° C. to about 120° C., about 40° C. to about 100° C., about 50° C. to about 80° C., about 50° C. to about 70° C., about 55° C. to about 65° C., or about 60° C.

154. A process according to clause 152 or clause 153, wherein the drying is for a period of time of: about 6 hours to about 48 hours, about 10 hours to about 40 hours, about 18 to about 30 hours, about 20 to about 28 hours, or about 24 hours.

155. A product obtainable by the process of any of clauses 133, 134, 135, 136, 137, 138, 139, 140, 141, 142, 143, 144, 145, 146, 147, 148, 149, 150, 151, 152, 153, or 154.

156. A process for preparing a product as defined in any of clauses 124, 125, 126, 127, 128, 129, 130, 131, 132, or 133, comprising stirring Trilaciclib dihydrochloride in an organic solvent (preferably wherein the organic solvent is, or comprises, a mixture of acetonitrile and an alcohol, more particularly wherein the alcohol is a $C_{1-6}$ alcohol, particularly methanol, ethanol or isopropanol, and especially isopropanol.

157. A process according to clause 156, wherein the vol/vol ratio of acetonitrile to alcohol (preferably isopropanol) may be: about 200:1 to about 10:1, about 180:1 to about 50:1, about 150:1 to about 60:1, about 120:1 to about 80:1, about 110:1 to about 90:1, or about 100:1.

158. A process according to clause 156 or clause 157, wherein the mixture is stirred at a temperature of: about −5° C. to about 15° C., about −2° C. to about 10° C., or about 0° C. to about 5° C.

159. A process according to any of clauses 156, 157 or 158, wherein the stirring is for a period of time of: about 6 hours to about 48 hours, about 10 hours to about 40 hours, about 15 hours to about 30 hours, about 18 hours to about 24 hours, or about 20 hours.

160. A process according to any of clauses 156, 157, 158, or 159, wherein the mixture of Trilaciclib dihydrochloride in a solvent comprising acetonitrile and an alcohol is prepared by combining Trilaciclib in a solution with acetonitrile, with a solution of hydrochloric acid the alcohol (preferably isopropanol).

161. A process according to clause 160, wherein the hydrochloric acid is in the form of hydrogen chloride gas in alcohol solvent, particularly wherein the alcohol solvent is a $C_{1-6}$ alcohol, and more particularly isopropanol.

162. A process according to clause 160 or clause 161, wherein the hydrochloric acid (hydrogen chloride gas in alcohol) is added to the Trilaciclib solution.
163. A process according to any of clauses 156, 157, 158, 159, 160, 161, or 162, further comprising isolating the Trilaciclib dihydrochloride Form THCl6, optionally by centrifugation, decantation, or filtration, preferably filtration.
164. A process according to clause 163, further comprising drying the product, preferably under reduced pressure.
165. A process according to clause 164, wherein the drying is carried out at elevated temperature, preferably at a temperature of: about 18° C. to about 50° C., about 20° C. to about 40° C., about 22° C. to about 30° C., or about 25° C.
166. A process according to clause 164 or clause 165, wherein the drying is carried out for about 2 to about 60 minutes, about 5 to about 30 minutes, about 10 to about 15 minutes.
167. A product obtainable by the process of any of clauses 156, 157, 158, 159, 160, 161, 162, 163, 164, 165, or 166
168. A crystalline polymorph of Trilaciclib hydrobromide salt, designated Form THBr1, which is characterized by data selected from one or more of the following: an X-ray powder diffraction pattern substantially as depicted in FIG. 17; an X-ray powder diffraction pattern having peaks at 6.5, 8.6, 17.2, 19.5 and 26.8 degrees 2-theta±0.2 degrees 2-theta; and combinations of these data.
169. Crystalline Form THBr1 of Trilaciclib hydrobromide salt according to clause 168, which is characterized by an X-ray powder diffraction pattern having peaks at 6.5, 8.6, 17.2, 19.5 and 26.8 degrees 2-theta±0.2 degrees 2-theta, and also having any one, two, three or four additional peaks selected from 18.7, 25.2, 28.1 and 29.9 degrees 2-theta±0.2 degrees 2-theta.
170. Crystalline Form THBr1 of Trilaciclib hydrobromide salt according to clause 168 or clause 169, which is characterized by an X-ray powder diffraction pattern having peaks at 6.5, 8.6, 17.2, 18.7, 19.5, 25.2, 26.8, 28.1, and 29.9 degrees 2-theta±0.2 degrees 2-theta.
171. Crystalline Form THBr1 of Trilaciclib hydrobromide salt according to any of clauses 168, 169 or 170, wherein the mole ratio of Trilaciclib to hydrobromic acid is 1.1.
172. Crystalline Form THBr1 of Trilaciclib hydrobromide salt according to any of clauses 168, 169, 170, or 171, which is isolated.
173. Trilaciclib hydrobromide salt.
174. Trilaciclib hydrobromide salt according to clause 173, wherein the mole ratio of Trilaciclib to hydrobromic acid is 1:1.
175. A product according to any of according to any of clauses 124, 125, 126, 127, 129, 130, 131, or 132, which is a hydrate, optionally a hemihydrate, a monohydrate, a dihydrate, a trihydrate, a tetrahydrate, a pentahydrate, or a hexahydrate.
176. A product according to any of clauses 1-66, 82-131, 155, and 167-175, which is substantially polymorphically pure.
177. A product according to clause 176, which contains 20% (w/w) or less, about 10% (w/w) or less, about 5% (w/w) or less, about 2% (w/w) or less, about 1% (w/w) or less, or about 0% of any other forms of the subject compound.
178. A crystalline product according to clause 176, which contains 20% (w/w) or less, about 10% (w/w) or less, about 5% (w/w) or less, about 2% (w/w) or less, about 1% (w/w) or less, or about 0% of any other crystalline forms of the subject compound.
179. A crystalline product according to clause 177, or clause 178, which contains 20% (w/w) or less, about 10% (w/w) or less, about 5% (w/w) or less, about 2% (w/w) or less, about 1% (w/w) or less, or about 0% of amorphous forms of the subject compound.
180. Use of a product according to any of clauses 1-66, 82-133, 155, and 167-175, for preparing other crystalline forms of Trilaciclib, salts of Trilaciclib or crystalline forms thereof, or solvates of Trilaciclib or crystalline forms thereof.
181. Use of a product according to any of clauses 1-66, 82-133, 155, and 167-175, for preparing pharmaceutical compositions of Trilaciclib or Trilaciclib salts.
182. A pharmaceutical composition comprising a product according to any of clauses 1-66, 82-133, 155, and 167-175, and at least one pharmaceutically acceptable excipient.
183. Use of a product according to any of clauses 1-66, 82-133, 155, and 167-175, for the preparation of a pharmaceutical composition and/or formulation, optionally wherein the composition is in the form of a solution for injection or infusion, or in the form of a powder for solution for injection or for infusion.
184. A process for preparing the pharmaceutical composition according to clause 182, comprising combining a product according to any of clauses 1-66, 82-133, 155, and 167-175, with at least one pharmaceutically acceptable excipient.
185. A product according to any of clauses 1-66, 82-133, 155, and 167-175, or a pharmaceutical composition according to clause 182, for use as a medicament.
186. A product according to any of clauses 1-66, 82-133, 155, and 167-175, or a pharmaceutical composition according to clause 182, for use as a chemo protective agent; in particular to reduce chemotherapy-induced bone marrow suppression in patients with: small cell lung cancer (SCLC), non-small cell lung cancer (NSCLC), colorectal cancer (particularly metastatic colorectal cancer), breast cancer (particularly metastatic triple-negative breast cancer), and bladder cancer (particularly advanced/metastatic bladder cancer); and preferably in patients with SCLC.

186. A method of treating chemotherapy-induced bone marrow suppression comprising administering a therapeutically effective amount of a product according to any of clauses 1-66, 82-133, 155, and 167-175, or a pharmaceutical composition according to clause 182, to a subject in need of the treatment.

The invention claimed is:

1. A crystalline form of Trilaciclib dihydrochloride salt, designated Form THCl6, which is characterized by data selected from the following:

(a) an X-ray powder diffraction pattern substantially as depicted in FIG. 16; or (b) an X-ray powder diffraction pattern having peaks at 7.3, 18.9, 23.3, 27.7 and 29.2 degrees 2-theta 0.2 degrees 2-theta.

2. The crystalline form of Trilaciclib dihydrochloride salt according to claim 1, which is further characterized by an X-ray powder diffraction pattern having any one, two, three or four additional peaks selected from 8.1, 13.5, 16.2 and 21.1 degrees 2-theta 0.2 degrees 2-theta.

3. The crystalline form of Trilaciclib dihydrochloride salt according to claim 1 which is characterized by an XRPD pattern having peaks at 7.3, 8.1, 13.5, 16.2, 18.9, 21.1, 23.3, 27.7 and 29.2 degrees 2-theta 0.2 degrees 2-theta.

4. The crystalline form of Trilaciclib dihydrochloride salt according to claim 1 containing about 20% (w/w) or less of any other forms of Trilaciclib or salts thereof.

5. A crystalline form of Trilaciclib citrate salt designated Form TCT1, which is characterized by an X-ray powder diffraction pattern substantially as depicted in FIG. 8; or an X-ray powder diffraction pattern having peaks at 6.1, 7.3, 11.3, 15.3 and 19.3 degrees 2-theta 0.2 degrees 2-theta.

6. The crystalline form of Trilaciclib citrate salt according to claim 5, which is further characterized by an X-ray powder diffraction pattern having peaks at 6.1, 7.3, 11.3, 15.3 and 19.3 degrees 2-theta+0.2 degrees 2-theta, and also having any one, two, three or four additional peaks selected from 8.9, 9.3, 20.4 and 22.7 degrees 2-theta+0.2 degrees 2-theta.

7. The crystalline form of Trilaciclib citrate salt according to claim 5, which is characterized by an X-ray powder diffraction pattern having peaks at 6.1, 7.3, 8.9, 9.3, 11.3, 15.3, 19.3, 20.4, and 22.7 degrees 2-theta 0.2 degrees 2-theta.

8. The crystalline form of Trilaciclib citrate salt according to claim 5, containing about 20% (w/w) or less of any other forms of Trilaciclib or salts thereof.

9. A pharmaceutical composition comprising the crystalline Trilaciclib dihydrochloride salt according to claim 1, and at least one pharmaceutically acceptable excipient.

10. A process for preparing a pharmaceutical composition comprising combining the crystalline Trilaciclib dihydrochloride salt according to claim 1 with at least one pharmaceutically acceptable excipient.

11. A medicament comprising the crystalline form of Trilaciclib dihydrochloride salt according to claim 1.

12. A method of treating chemotherapy-induced bone marrow suppression comprising administering a therapeutically effective amount of the crystalline form of Trilaciclib dihydrochloride salt according to claim 1 to a subject in need of the treatment.

13. A pharmaceutical composition comprising the crystalline form of Trilaciclib citrate salt according to claim 5, and at least one pharmaceutically acceptable excipient.

14. A process for preparing a pharmaceutical composition comprising combining the crystalline form of Trilaciclib citrate salt according to claim 5 with at least one pharmaceutically acceptable excipient.

15. A medicament comprising the crystalline Trilaciclib citrate salt according to claim 5.

16. A method of treating chemotherapy-induced bone marrow suppression comprising administering a therapeutically effective amount of the crystalline Trilaciclib citrate salt according to claim 5 to a subject in need of the treatment.

* * * * *